US010336994B2

(12) United States Patent
Toplak et al.

(10) Patent No.: US 10,336,994 B2
(45) Date of Patent: Jul. 2, 2019

(54) SUBTILISIN VARIANTS HAVING A MUTATION IN THE S2 OR S2# POCKET

(71) Applicant: EnzyPep B.V., Geleen (NL)

(72) Inventors: Ana Toplak, Eindhoven (NL); Timo Nuijens, Valkenburg (NL); Peter Jan Leonard Mario Quaedflieg, Elsloo (NL)

(73) Assignee: ENZYPEP B.V., Geleen (NL)

( * ) Notice: Subject to any disclaimer, the term of this patent is extended or adjusted under 35 U.S.C. 154(b) by 0 days.

(21) Appl. No.: 16/193,963

(22) Filed: Nov. 16, 2018

(65) Prior Publication Data

US 2019/0078069 A1 Mar. 14, 2019

Related U.S. Application Data

(63) Continuation of application No. PCT/NL2018/050332, filed on May 18, 2018.

(30) Foreign Application Priority Data

May 19, 2017 (EP) .................................... 17171981

(51) Int. Cl.
| | | |
|---|---|---|
| *C12N 9/52* | (2006.01) | |
| *C12P 21/02* | (2006.01) | |
| *C07K 1/02* | (2006.01) | |
| *C12N 9/54* | (2006.01) | |
| *C12P 21/06* | (2006.01) | |

(52) U.S. Cl.
CPC ................ *C12N 9/52* (2013.01); *C07K 1/026* (2013.01); *C12N 9/54* (2013.01); *C12P 21/02* (2013.01); *C12P 21/06* (2013.01); *C12Y 304/21062* (2013.01)

(58) Field of Classification Search
CPC .... C12N 9/52; C12P 21/02; C12Y 304/21062
See application file for complete search history.

(56) References Cited

U.S. PATENT DOCUMENTS 6,541,235 B1 * 4/2003 Bryan ................... C11D 3/386
435/221

FOREIGN PATENT DOCUMENTS

| WO | 9627671 A1 | 9/1996 |
| WO | 9949013 A2 | 9/1999 |
| WO | 2016056913 A1 | 4/2016 |

OTHER PUBLICATIONS

Moree et al., "Exploitation of Subtilisin BPN as Catalyst for the Synthesis of Peptides Containing Noncoded Amino Acids, Peptide Mimetics and Peptide Conjugates", J. Am. Chem. Soc., 1997, vol. 119, No. 17, pp. 3942-3947.
Nuijens et al., "Chemo-enzymatic peptide synthesis (CEPS) using omniligases and selective peptiligases", Chemistry Today, 2016, vol. 34, pp. 16-19.
Nuijens et al., "Engineering a Diverse Ligase Toolbox for Peptide Segment Condensation", Advanced Synthesis & Catalysis, 2016, vol. 358, No. 24, pp. 4041-4048.
Search Report for European Patent Application No. 17171931.8 (8 Pages) (dated Nov. 2, 2017).

* cited by examiner

*Primary Examiner* — Karen Cochrane Carlson
(74) *Attorney, Agent, or Firm* — Lucas & Mercanti, LLP

(57) ABSTRACT

The invention relates to a subtilisin BPN' variant or homolog thereof, having the following mutations compared to subtilisin BPN' represented by SEQUENCE ID NO: 2 or a homolog sequence thereof:—a deletion of the amino acids corresponding to positions 75-83;—a mutation at the amino acid position corresponding to S221, the mutation corresponding to S221C or S221 selenocysteine, preferably S221C;—at least one further mutation selected from the group consisting of amino acid positions corresponding to F189W, F189Y, S33D, S33T, N218D, N218T, N218E, N62D, N62S, N62W, and N62Y; preferably a mutation at the amino acid position corresponding to P225; wherein the amino acid positions are defined according to the sequence of subtilisin BPN' represented by SEQUENCE ID NO: 2. The invention further relates to enzymatically synthesizing a peptide.

29 Claims, 5 Drawing Sheets

Specification includes a Sequence Listing.

SUBTILISIN VARIANTS HAVING A MUTATION IN THE S2 OR S2# POCKET

CROSS-REFERENCE TO RELATED APPLICATIONS

This application is a Continuation of PCT/NL2018/050332, filed May 18, 2018 which claims the benefit of European Patent Application No. 17171981.8, filed May 19, 2017, the contents are incorporated herein by reference.

FIELD OF THE INVENTION

The invention relates to an enzyme, which enzyme is a subtilisin BPN' variant or homologue thereof. The invention further relates to a method for enzymatically synthesising a peptide, wherein use is made of said enzyme.

Peptides have many applications, for instance as pharmaceutical, food or feed ingredient, or cosmetic ingredient.

Processes for synthesizing peptides are generally known in the art. Oligopeptides can be chemically synthesized in a stepwise fashion in solution or on the solid phase via highly optimized processes. However, peptides longer than 10-15 amino acids are often very difficult to synthesize due to side reactions and as a consequence purification is troublesome. Therefore, peptides longer than 10 amino acids are often synthesized by a combination of solid-phase synthesis of side-chain protected oligopeptide fragments which are subsequently chemically condensed in solution, e.g. as in a 10+10 condensation to make a peptide of 20 amino acids. The major drawback of chemical side-chain protected oligopeptide fragment condensation is that upon activation of the C-terminal amino acid residue of the acyl donor racemisation occurs. In contrast, enzyme-catalysed peptide couplings are completely devoid of racemisation and have several other advantages over chemical peptide synthesis such as the absence of side reactions on the side-chain functionalities. For industrial application, an enzymatic peptide synthesis concept based on a kinetic approach, i.e. using an acyl donor C-terminal ester is most attractive (see for instance N. Sewald and H.-D. Jakubke, in: "Peptides: Chemistry and Biology", 1st reprint, Ed. Wiley-VCH Verlag GmbH, Weinheim 2002).

Chemo-enzymatic peptide synthesis can entail the enzymatic coupling of oligopeptide fragments which have individually been synthesized using chemical synthesis, fermentation, or by a combination of chemical and enzymatic coupling steps. Some reports have been published on the enzymatic condensation of oligopeptide fragments in aqueous solution (Kumaran et al. Protein Science, 2000, 9, 734; Björup et al. Bioorg. Med. Chem. 1998, 6, 891; Homandberg et al. Biochemistry, 1981, 21, 3387; Komoriya et al. Int. J. Pep. Prot. Res. 1980, 16, 433).

It was found by Wells et al. (U.S. Pat. No. 5,403,737) that the condensation of oligopeptides in aqueous solution could be significantly improved by altering the active site of subtilisin BPN', a subtilisin from *B. amyloliquefaciens* (SEQ ID NO: 2). When two mutations were introduced, i.e. S221C and P225A, a subtilisin BPN' variant called subtiligase was obtained having a 500-fold increased synthesis over hydrolysis ratio (S/H ratio) as compared to wild-type subtilisin BPN'. In further experiments Wells et al. added five additional mutations to subtiligase, i.e. M50F, N76D, N109S, K213R and N218S, to make the enzyme more stable (Proc. Natl. Acad. Sci. USA, 1994, 91, 12544). The new mutant called stabiligase appeared moderately more resistant to sodium dodecasulphate and guanidinium hydrochloride, but hydrolysis was still a major side reaction. For instance a peptide carboxyamidomethyl-ester (Cam-ester) was ligated to an peptide amine using stabiligase in a yield of 44%. In this example, 10 equivalents of the peptide C-terminal ester were used and thus, 9.56 equivalents of the peptide C-terminal ester were hydrolyzed at the C-terminal ester functionality and only 0.44 equivalents ligated to the peptide amine to form the product. Probably for this reason, the past 20 years subtiligase nor stabiligase have been industrially applied in enzymatic peptide synthesis, to the best of the inventors knowledge.

In WO 2016/056913 a solution is provided for the undesirably high hydrolytic activity encountered with enzymes like subtiligase or stabiligase when used for peptide synthesis in an aqueous environment, by providing a subtilisin BPN' variant or a homologue thereof, which comprises the following mutations compared to subtilisin BPN' represented by SEQ ID NO: 2 or a homologue sequence thereof: a deletion of the amino acids corresponding to positions 75-83, a mutation at the amino acid position corresponding to S221, the mutation being S221C or S221 selenocysteine, and preferably one or more further mutations. In particular, said enzymes are useful in enzymatic methods to prepare peptides by condensation of two peptide fragments or by cyclisation of a peptide, providing an improved synthesis over hydrolysis (S/H) ratio and stability compared to subtilisin BPN' in an aqueous reaction medium. Also, a method is disclosed wherein a protein is effectively coupled to another peptide.

There remains a need for further enzymes that can be used in the enzymatic synthesis of peptides by fragment condensation or cyclisation. In general, such need exists in particular in order to broaden the palette of tools for making specific peptides.

In particular, there is a need to provide further subtilisin BPN' variants or homologues thereof, which offer a broad substrate scope for the peptide acyl donor and the peptide nucleophile, whilst maintaining or improving the S/H ratio.

SUMMARY OF THE INVENTION

It has now been found that this need is met by providing enzymes with one or more specific mutations in the penultimate pockets to the coupling site, i.e. in the S2' pocket and/or in the S2 pocket of a subtilisin BPN' variant or homologues thereof. In particular, the one or more specific mutations in the S2' pocket broaden the substrate scope not only for the P2' position of the peptide nucleophile but also for the P1' position of the peptide nucleophile. In particular, the one or more specific mutations in the S2 pocket broaden the substrate scope not only for the P2 position of the peptide acyl donor, but also for the P1' and P2' positions of the peptide nucleophile.

Accordingly, the invention relates to an enzyme, which enzyme is a subtilisin BPN' variant or homologue thereof, comprising the following mutations compared to subtilisin BPN' represented by SEQ ID NO: 2 or a homologue sequence thereof:
  a deletion of the amino acids corresponding to positions 75-83;
  a mutation at the amino acid position corresponding to S221, the mutation being S221C or S221 selenocysteine, preferably S221C;
  at least one further mutation selected from the group consisting of amino acid positions corresponding to F189W, F189Y, S33D, S33T, N218D, N218T, N218E, N62D, N62S, N62W, and N62Y; and preferably a mutation at the amino acid position corresponding to P225;
wherein the amino acid positions are defined according to the sequence of subtilisin BPN' represented by SEQ ID NO: 2.

The enzyme according to the invention is useful as a catalyst. The enzyme generally has catalytic activity with respect to the formation of a peptide bond (condensation activity). In particular, the enzyme has ligase activity or cyclase activity.

Accordingly, the invention further relates to a method for enzymatically synthesizing a peptide, comprising coupling (a) a peptide C-terminal ester or thioester and (b) a peptide nucleophile having an N-terminally unprotected amine, wherein the coupling is carried out in a fluid comprising water, and wherein the coupling is catalyzed by an enzyme according to the invention.

Accordingly, the invention further relates to a method for enzymatically synthesizing a cyclic peptide of at least 12 amino acids, comprising subjecting a peptide C-terminal ester or thioester having an N-terminally unprotected amine to a cyclisation step wherein said cyclization is carried out in a fluid comprising water, and wherein the cyclization is catalyzed by an enzyme according to the invention.

The invention provides a useful alternative to known methods of preparing peptides, including proteins extended with a peptide and peptide-conjugates.

In particular an enzyme according to the invention has catalytic activity in the formation of a peptide bond with a high S/H ratio, typically more than 1, preferably 2 or more, in particular 5 or more, in particular in a reaction medium comprising water, more in particular an aqueous medium. The upper value of this quotient is not critical; in practice it may e.g. be 100 or less, in particular 20 or less.

The invention in particular provides enzymes with a broad(er) substrate scope, whilst at least substantially maintaining or improving the S/H ratio, in particular in an aqueous reaction medium.

BRIEF DESCRIPTION OF THE FIGURES

FIG. 1 B: The P2' substrate scope of BS149-DMPH and BS149-DMPH+F189W.
FIG. 1 C: The P2' substrate scope of BS149-DMPHNV and BS149-DMPHNV+F189W
FIG. 1 D: The P1' substrate scope of BS149-DMPHNV and BS149-DMPHNV+F189W

DETAILED DESCRIPTION OF THE INVENTION

Figure 1A:
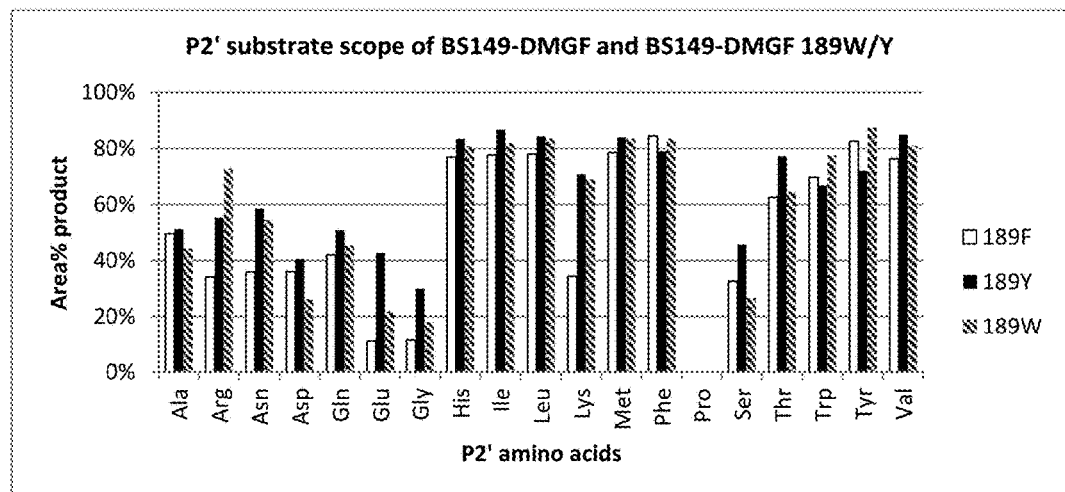
FIG. 1 A: The P2' substrate scope of BS149-DMGF and BS149-DMGF+F189W/Y.

For the purpose of this invention, with "synthesis over hydrolysis ratio" (S/H ratio) is meant the amount of enzymatically synthesised (oligo)peptide product divided by the amount of (oligo)peptide C-terminal ester or thioester of which the ester or thioester group has been hydrolysed. For further details on determining an S/H ratio, reference is made to WO 2016/056913.

The S/H ratio of an enzyme according to the invention divided by the S/H ratio of subtilisin BPN'—at least under the conditions described in the examples—is usually more than 100, preferably 250 or more, more preferably 500 or more, in particular 1000 or more. The upper value of this quotient is not critical; it may approximate infinity.

The term "or" as used herein is defined as "and/or" unless it is specified otherwise or it follows from the context that it means 'either . . . or . . . '.

The term "a" or "an" as used herein is defined as "at least one" unless it is specified otherwise or it follows from the context that it should refer to the singular only.

When referring to a noun (e.g. a compound, an additive, etc.) in the singular, the plural is meant to be included, unless it follows from the context that it should refer to the singular only.

In the context of this application, the term "about" means in particular a deviation of 10% or less from the given value, more in particular 5% or less, even more in particular 3% or less.

The term "essential(ly)" or "(at least) substantial(ly)" is generally used herein to indicate that it has the general character or function of that which is specified. When referring to a quantifiable feature, this term is in particular used to indicate that it is at least 75%, more in particular more than 90%, even more in particular more than 98% of the maximum of that feature. The term "essentially free" is generally used herein to indicate that a substance is not present (below the detection limit achievable with analytical methodology as available on the effective filing date) or present in such a low amount that it does not significantly affect the property of the product that is essentially free of said substance. In practice, in quantitative terms, a product is usually considered essentially free of a substance, if the content of the substance is 0-0.1 wt. %, in particular 0-0.01 wt. %, more in particular 0-0.005 wt. %, based on total weight of the product in which it is present.

When referring to a compound of which stereoisomers exist, the compound may be any of such stereoisomers or a mixture thereof. Thus, when referred to, e.g., an amino acid of which enantiomers exist, the amino acid may be the L-enantiomer, the D-enantiomer or a mixture thereof. In case a natural stereoisomer exists, the compound is preferably a natural stereoisomer.

The term 'pH' is used herein for the apparent pH, i.e. the pH as measured with a standard, calibrated pH electrode.

For the purpose of this invention, with "peptides" is meant any chain composed of two or more amino acids. Thus, peptides are generally amides at least conceptually composed of two or more amino carboxylic acid molecules (i.e. amino acids) by formation of a covalent bond from the carbonyl carbon of one to the nitrogen atom of another with formal loss of water. The term 'peptide' includes oligopeptides and polypeptides. The term 'peptide' is usually applied to structures formed from alpha-amino acids, although a peptide may comprise other amino acids, such as one or more beta-amino acids and/or one or more gamma-amino acids. A peptide may be linear, branched or cyclic. A peptide can have a single chain composed of two or more amino acids or a peptide can have a plurality of chains (i.e. a chimeric peptide). In the case a peptide is composed of two or more chains, each chain generally is composed of three or more amino acid molecules.

The amino acid sequence of a peptide is referred to as the primary structure.

In an embodiment, the peptide is essentially free of a secondary structure and essentially free of a tertiary structure.

In a further embodiment, the peptide has a secondary structure. Secondary structures are generally highly regular local sub-structures, such as alpha-helices and beta-sheets (or beta-strands), by interactions between the individual amino acids and the peptide backbone.

In an embodiment, the peptide (which may be a chimeric peptide) has a tertiary structure. Tertiary structures are generally formed by multiple interactions, among others hydrogen bonding, hydrophobic interactions, van der Waals interactions, ionic interactions and disulphide bonds. The secondary structure can also contribute to the tertiary structure. The tertiary structure provides a three-dimensional shape (which is essentially fixed in a stable environment, such as in the absence of a change in temperature and in the absence of a change in the medium wherein the peptide is present, etc.). As the skilled person knows, the tertiary structure is different from a random coil peptide chain lacking any fixed three-dimensional structure. Proteins, like insulin, albumin, antibodies, peptide-based receptor ligands, are examples of peptides having a tertiary structure. Also various peptide-based hormones have a tertiary structure. Examples thereof include erythropoietin EPO and peptide-based growth factors.

Disulphide bonds (disulphide bridges) are typically bonds between two cysteine units (formed by oxidation). Thus, two amino acids in a same peptide chain (amino acid sequence) can be covalently bound, also if they are not adjacent amino acids in the amino acid sequence. Also, a disulphide bond between a first cysteine of a first peptide chain and a second cysteine of a second peptide chain, which may have the same or a different amino acid sequence, can be formed to form a peptide. Such peptide comprises more than one peptide chain. An example of a peptide composed of more than one peptide chain, wherein the different chains are bound via a disulphide bond is insulin.

In an embodiment, a peptide (to be) coupled or cyclised essentially consists of amino acid units. In a further embodiment, a peptide (to be) coupled or cyclised essentially consists of amino acid units and protective groups.

In an embodiment, a peptide to be coupled or cyclised is a conjugate of a peptide chain of two or more amino acids and another residue, such as a carbohydrate or a fatty acid. These peptides are called glycopeptides and lipopeptides respectively. Fatty acids can e.g. be used to change the solubility. Examples of suitable fatty acids, are C8-C24 saturated fatty acids and C8-C24 unsaturated fatty acids.

In a further embodiment, a peptide (to be) coupled or cyclised is a peptide modified with a synthetic hydrophilic polymer, such as a polyalkylene glycol. Particularly preferred polyalkylene glycols are polyethylene glycols. Such polymers can, e.g. be used to increase the solubility or the in vivo half-life (such as in blood plasma).

In a further embodiment, a peptide (to be) coupled or cyclised is a conjugate of a peptide and a polysialic acid.

A peptide (to be) coupled or cyclised may be a conjugate of a peptide and an imaging agent, a radio-therapeutic agent, a toxin or another non-peptidic agent, e.g. a chelating agent or a non-peptidic biologically active moiety.

In an embodiment, the peptide C-terminal (thio)ester and/or the peptide nucleophile is a biologically active peptide, e.g. an insulin receptor ligand or a hormone. Preferred insulin receptor ligands are human insulin, porcine insulin, Humalog, aspart, insulin glulisine, insulin detemir, insulin degludec, and glargine insulin.

Preferred hormones are growth factors.

Further, preferred examples of biologically active peptides that can be synthesised in accordance with the invention or that can be used as a substrate in a coupling reaction according to the invention include Exenatide, Exenatide analogues (such as an analogue selected from the group of Glp-1, Teduglutide, Glucagon, Lixisenatide, Liraglutide and Semaglutide), Thymosin-alpha-1, Thymosin-alpha-1 analogues, Teriparatide, peptides comprising the sequence of any of these and one or more further amino acid units. A conjugate comprising Exenatide, Lixisenatide or an analogue thereof can be used in the treatment of type 2 diabetes mellitus, in particular as adjunctive therapy to improve glycemic control in patients with type 2 diabetes mellitus who are taking metformin, but have not achieved adequate glycemic control. A conjugate comprising Thymosin-alpha-1 or an analogue thereof can be used in a patient benefiting from enhancing cell-mediated immunity. Particularly suitable synthesis methods in accordance with the invention for one or more of these pharmaceutical peptides can be based on the present disclosure, optionally in combination with PCT/NL2016/050501 or WO 2016/056913.

In an embodiment, the method for enzymatically synthesising a peptide is used to synthesise a peptide containing an imaging agent moiety (e.g. chromogenic, fluorescent, phosphorescent, radioactive), a radio-therapeutic moiety or a biologically active peptide and containing a protein for targeted delivery of the first peptide to a specific site, e.g. to specific organ tissue. In such embodiment the protein is coupled to a another peptide containing the imaging agent moiety, the radio-therapeutic moiety or the biologically active peptide. Either one of these can be the peptide nucleophile respectively the peptide C-terminal ester or thioester.

Well known examples of proteins, suitable for such purpose, are antibodies, in particular immunoglobulins or parts thereof, such as an antigen-binding fragment (Fab) of an immunoglobulin or a single-domain antibody (nanobody). Specific examples of antibodies that can be coupled in accordance with the invention are IgG, IgA, IgE, IgM and IgD.

In an embodiment, a protein suitable to increase the half-life of another (biologically active) peptide is coupled to the other (biologically active) peptide, in particular to increase the blood plasma half-life of that (biologically active) peptide. Albumins are examples of proteins that can be coupled to increase the half-life of another (biologically active) peptide. Either one of these can be the peptide nucleophile respectively the peptide C-terminal ester or thioester.

Typically, a peptide—which term includes oligopeptides, proteins and chimeric peptides—comprises up to about 35 000 amino acid units, in particular 3-20 000 amino acid units, more in particular 4-5 000 amino acid units, preferably 6-1000 amino acid units. In a specifically preferred embodiment the peptide comprises 500 amino acid units or less, in particular 200 or less, more in particular 100 or less. In a specifically preferred embodiment, the peptide comprises at least 10 amino acid units, more specifically at least 15 amino acids, at least 25 amino acids or at least 40 amino acids.

With "oligopeptides" is meant within the context of the invention, a peptide composed of 2-200 amino acid units, in particular composed of 5-100 amino acid units, more in particular composed of 10-50 amino acid units.

For the purpose of this invention, with "peptide bond" is meant the amide bond between (i) either the alpha-amino terminus of one alpha-amino acid or the beta-amino terminus of one beta-amino acid and (ii) either the alpha-carboxyl terminus of one other alpha-amino acid or the beta-carboxyl terminus of one other beta-amino acid. Preferably, the peptide bond is between the alpha-amino terminus of one alpha-amino acid and the alpha-carboxyl terminus of another alpha-amino acid.

For the purpose of this invention, with "cyclic peptide" is meant a peptide chain wherein the alpha-amino terminus and the alpha-carboxyl terminus of a branched or linear peptide are linked via a peptide bond, thereby forming a ring structure of at least 12 amino acid units. The cyclic peptide is in particular composed of 12-200 amino acid units, more in particular composed of 12-100 amino acid units and preferably composed of 12-50 amino acid units.

In the context of the invention with "amino acid sidechain" is meant any proteinogenic or non-proteinogenic amino acid side-chain.

Proteinogenic amino acids are the amino acids that are encoded by the genetic code. Proteinogenic amino acids include: alanine (Ala), valine (Val), leucine (Leu), isoleucine (Ile), serine (Ser), threonine (Thr), methionine (Met), cysteine (Cys), asparagine (Asn), glutamine (Gln), tyrosine (Tyr), tryptophan (Trp), glycine (Gly), aspartic acid (Asp), glutamic acid (Glu), histidine (His), lysine (Lys), arginine (Arg), proline (Pro) and phenylalanine (Phe). Selenocysteine (Sec, U) is an amino acid, of which the structure corresponds to cysteine, with the proviso that it contains a selenium instead of a sulphur atom. Proteinogenic amino acids are the L-stereoisomers of said amino acids (except for glycine, which does not have a stereo-isomeric form).

Non-proteinogenic amino acids may in particular be selected amongst D-amino acids, L- or D-phenylglycine, DOPA (3,4-dihydroxy-L-phenylalanine), beta-amino acids, 4-fluoro-phenylalanine, or $C^{\alpha}$-alkylated amino acids.

The term "(thio)ester" is used herein as short-hand for the phrase "ester or thioester".

The term "mutated" or "mutation" as used herein regarding proteins or polypeptides—in particular enzymes— means that at least one amino acid in the wild-type or naturally occurring protein or polypeptide sequence has been replaced with a different amino acid, inserted into, appended to, or deleted from the sequence via mutagenesis of nucleic acids encoding these amino acids. Mutagenesis is a well-known method in the art, and includes, for example, site-directed mutagenesis by means of PCR or via oligonucleotide-mediated mutagenesis as described in Sambrook et al., Molecular Cloning—A Laboratory Manual, 2nd ed., Vol. 1-3 (1989). The term "mutated" or "mutation" as used herein regarding genes means that at least one nucleotide in the nucleic acid sequence of that gene or a regulatory sequence thereof, has been replaced with a different nucleotide, has been inserted into, has been appended to, or has been deleted from the sequence via mutagenesis, resulting in the transcription of a protein sequence with a qualitatively of quantitatively altered function or resulting in the knock-out of that gene.

In the present specification, a shorthand for denoting amino acid substitutions employs the single letter amino acid code of the amino acid that is substituted, followed by the number designating where in the protein amino acid sequence the substitution is made. This number is the amino acid position of the wild-type amino acid sequence. Thus for the mutated amino acid sequence it is the amino acid position corresponding to the position with that number in the wild type enzyme. Due to one or more other mutations at a lower position (additions, insertions, deletions, etc.) the actual position does not need to be the same. The skilled person will be able to determine the corresponding positions using a generally known alignment technique, such as NEEDLE. The number is followed by the single letter code of the amino acid that replaces the wild-type amino acid therein. For example, F189W denotes the substitution of phenylalanine at the position corresponding to position 189 to tryptophan. X is used to indicate any other proteinogenic amino acid than the amino acid to be substituted. For example, F189X denotes the substitution of phenylalanine at the position corresponding to position 189 to any other proteinogenic amino acid.

The term "ligase" is used herein for an enzyme having catalytic activity in the coupling of two peptides by catalysing the formation of a peptide bond by coupling the C-terminus of a first peptide and the N-terminus of another peptide.

As defined by Schechter and Berger, the active site residues in proteases, including ligases are composed of contiguous pockets termed subsites. Each subsite pocket binds to a corresponding residue in the peptide substrate sequence, referred to here as the sequence position. According to this definition, amino acid residues in the substrate sequence are consecutively numbered outward from the cleavage sites as . . . -P4-P3-P2-P1-P1'-P2'-P3'-P4'- . . . (the scissile bond is located between the P1 and P1' positions), while the subsites (pockets) in the active site are correspondingly labelled as . . . -S4-S3-S2-S1-S1'-S2'-S3'-S4'-. (Schechter and Berger, Biochem Biophys Res Commun. 1967 Apr. 20; 27(2):157-62.)). It should be noted that not all proteases have all of said subsites. E.g. an S3' and/or an S4' pocket may be absent in a subtilisin BPN' variant or homologue thereof according to the invention.

For the purpose of this invention, with "S1, S2, S3 and S4 pocket" is meant the amino acids of a protease (in particular a ligase) which interact with the amino acids of a peptide acyl donor. The C-terminal amino acid ($1^{st}$ amino acid; P1) of the acyl donor peptide interacts with the amino acids in the S1 pocket of the protease. The penultimate amino acid ($2^{nd}$ amino acid from the C-terminal end; P2) of the acyl donor peptide interacts with the amino acids in the S2 pocket of the protease, the third amino acid (P3) with the S3 and the fourth amino acid (P4) with the S4 pocket. The S1-S4 binding pockets of a protease are defined by several amino acids which can be distant in the primary structure of the protease, but are close in the three dimensional space. For the purpose of this invention, with S1' and S2' pockets are meant the amino acids of a protease which interact with the N-terminal amino acids of a peptide nucleophile. The N-terminal amino acid of the peptide nucleophile interacts with the amino acids in the S1' pocket of the protease. The N-terminal penultimate amino acid of the peptide nucleophile interacts with the amino acids in the S2' pocket of the protease. The S1' and S2' binding pockets of a protease are defined by several amino acids which can be distant in the primary structure of the protease, but are close in the three dimensional space.

When an enzyme is mentioned with reference to an enzyme class (EC) between brackets, the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at www.chem.qmul.ac.uk/iubmb/enzyme/. Other suitable enzymes that have not (yet) been classified in a specified class but may be classified as such, are meant to be included.

Homologues typically have an intended function in common with the peptide or enzyme, of which it is a homologue, such as being capable of catalyzing the same reaction, in particular an enzymatic coupling or cyclisation reaction of a method according to the invention.

Amino acid or nucleotide sequences are said to be homologous when exhibiting a certain level of similarity. Whether two homologous sequences are closely related or more distantly related is indicated by "percent identity" or "percent similarity", which is high or low respectively.

The terms "homology", "percent homology", "percent identity" or "percent similarity" are used interchangeably herein. For the purpose of this invention, it is defined here that in order to determine the percent identity of two amino acid sequences, the complete sequences are aligned for optimal comparison purposes. In order to optimise the alignment between the two sequences gaps may be introduced in any of the two sequences that are compared. Such alignment is carried out over the full length of the sequences being compared. Alternatively, the alignment may be carried out over a shorter length, for example over about 20, about 50, about 100 or more nucleic acids or amino acids. The percentage identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, pp 443-453). The Needleman-Wunsch algorithm has been implemented in the computer program NEEDLE. For the purpose of this invention the NEEDLE program from the EMBOSS package was used (version 2.8.0 or higher, *EMBOSS: The European Molecular Biology Open Software Suite* (2000) Rice, P. Longden, I. and Bleasby, A. Trends in Genetics 16, (6) pp 276-277, emboss.bioinformatics.nl/). For protein sequences, EBLOSUM62 is used for the substitution matrix. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

The homology or identity between the two aligned sequences is calculated as follows: the number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity".

For purposes of the invention the level of identity (homology) between two sequences is calculated according to the definition of "longest-identity" as can be carried out by using the program NEEDLE.

The polypeptide sequences, in particular enzyme sequences, can further be used as a "query sequence" to perform a search against sequence databases, for example to identify other family members or related sequences. Such searches can be performed using the BLAST programs. Software for performing BLAST analyses is publicly available through the National Center for Biotechnology Information (www.ncbi.nlm.nih.gov). BLASTP is used for amino acid sequences. The BLAST program uses as defaults:

Cost to open gap: default=11 for proteins
Cost to extend gap: default=1 for proteins
Expect value: default=10
Wordsize: default=28 for megablast/3 for proteins Furthermore the degree of local identity (homology) between the amino acid sequence query and the retrieved homologous sequences is determined by the BLAST program. However only those sequence segments are compared that give a match above a certain threshold. Accordingly the program calculates the identity only for these matching segments. Therefore the identity calculated in this way is referred to as local identity.

The term "homologue" is used herein in particular for peptides, more in particular enzymes, having a sequence identity of at least 50%, preferably at least 60%, more preferably at least 70%, at least 80%, at least 90%, at least 95%, at least 96%, at least 97%, at least 98% or at least 99% with the peptide, in particular enzyme, with which the homologue peptide or enzyme is compared. Evidently, the sequence identity will be less than 100%. The percentage of sequence identity will depend on the number of mutations and the length of the peptide (enzyme) with which the homologue is compared. In 'longest identity' alignment deletions are not taken into account.

For the purpose of this invention, with "condensation" is meant the formation of a new amide bond between the C-terminal carboxylic function of a peptide) with the N-terminal amine function of a nucleophile, in particular another peptide.

The term "analogue" of a peptide is used in particular for peptides that are structural analogues and/or functional analogues of said peptide. Functional analogues have a same in vivo target (e.g. the same target receptor on a cell membrane); structural analogues have a high similarity in amino acid sequence. Functional analogues of a peptide may have a relatively low amino acid sequence identity, e.g. of about 50% or less over the full amino acid sequence, yet a high sequence identity (and thus a high structural similarity) with the peptide of which they are an analogue in a segment of the amino acid sequence, such as near the N-terminal part or near the C-terminal part. A structural analogue, in particular comprises an amino acid sequence that has at least 60%, more in particular at least 70%, preferably at least 80%, more preferably at least 90% sequence identity, more preferably at least 95% sequence identity with the amino acid sequence of the peptide of which a peptide is an analogue.

For the purpose of clarity and a concise description features are described herein as part of the same or separate embodiments, however, it will be appreciated that the scope of the invention may include embodiments having combinations of all or some of the features described. Terms used herein that are not specifically defined herein are as defined in WO 2016/056913, or—if not defined therein—used in accordance with common general knowledge.

The peptide C-terminal ester or thioester typically is an activated (thio)ester, i.e. it contains a carboxy ester or carboxy thioester group that can take part in the enzymatic coupling reaction. In principle, any (substituted or unsubstituted) alkyl or (substituted or unsubstituted) aryl (thio) ester can be used. Typical examples of (thio)esters which can take part in the enzymatic coupling reaction are methyl-, ethyl, propyl-, isopropyl-, phenyl-, benzyl- (such as p-carboxy-benzyl-), 2,2,2-trichloroethyl-, 2,2,2-trifluoroethyl-, cyanomethyl- and carboxyamidomethyl-(thio)esters.

Particularly good results have been obtained with carboxyamidomethyl-type esters represented by the formula peptide-(C=O)—O—$CX_1X_2$—C(=O)N—$R_1R_2$. Herein, each $X_1$ and $X_2$ independently represents a hydrogen atom or an alkyl group. Good results have been achieved when both $X_1$ and $X_2$ are a hydrogen atom (peptide-(C=O)—O—$CH_2$—C(=O)N—$R_1R_2$). Herein $R_1$ represents a hydrogen atom or an alkyl group and $R_2$ represents a hydrogen atom or an alkyl group or an amino acid or a peptide residue with a C-terminal carboxyamide or carboxylic acid functionality, optionally protected on the side-chain functionality of the amino acid or on one or more of the side-chain functionalities of the amino acids. Herein, each alkyl group may independently represent a (substituted or unsubstituted) C1-C7 alkyl group, preferably a (substituted or unsubstituted) linear C1-C6 alkyl group, more preferably a (substituted or unsubstituted) linear C1-C3 alkyl group, and most preferably a methyl group. Good results have in particular been achieved in a method of the invention wherein both $R_1$ and $R_2$ represent a hydrogen atom or wherein $R_1$ represents a hydrogen atom and $R_2$ represents an amino acid or peptide residue with a C-terminal carboxyamide or carboxylic acid functionality, optionally protected on the side-chain functionality of the amino acid or on one or more of the side-chain functionalities of the amino acids. Particularly good results have been achieved when using the Cam-ester, when $X_1$, $X_2$, $R_1$ and $R_2$ are a hydrogen atom.

Particularly good results have also been obtained with carboxyl substituted benzyl esters, in particular with p-carboxyl substituted benzyl esters represented by the formula peptide-(C=O)—O—$CH_2$—$C_6H_4$—$CO_2E$ wherein E represents a hydrogen atom, a positively charged salt ion such as an ammonium ion, or an amino acid or a peptide residue with a C-terminal carboxyamide or carboxylic acid functionality, optionally protected on the side-chain functionality of the amino acid or on one or more of the side-chain functionalities of the amino acids. Good results have also been obtained with p-carboxyl substituted benzyl esters represented by the formula peptide-(C=O)—O—$CH_2$—$C_6H_4$—$CO_2E$ wherein E is defined as above and in which one or more hydrogen atoms in the phenyl ring ($C_6H_4$ in the above formula) are replaced by a substituent, such as hydroxy, alkoxy, aryloxy or halogen.

The peptide C-terminal (thio)ester can be N-terminally unprotected or N-terminally protected.

The term 'N-terminal protection' is used herein to indicate that an N-terminal amine group of a peptide is provided with a protective group, generally at least substantially protecting the N-terminal amine group from being coupled to a C-terminal carboxylic group of another peptide or of the same peptide molecule.

In particular, good results have been achieved with a peptide C-terminal (thio)ester without protected side-chain functionalities.

In an embodiment, one or more side-chain functionalities (in particular hydroxyl groups, carboxyl groups or amine groups), e.g. all side-chain functionalities, are provided with a protecting group. In a preferred embodiment, only the side-chain functionalities of the amino acids at the P4 and P1 position of the peptide C-terminal (thio)ester (in particular hydroxyl groups, carboxyl groups or amine groups) are provided with a protecting group. Suitable protecting groups are known to the person skilled in the art. Carboxylic acid groups can for instance be protected with a cyclohexyl, benzyl or allyl group; amine functionalities can for instance be protected with an allyloxycarbonyl group or a trifluoroacetyl group.

The activated C-terminal (thio)ester group of the peptide C-terminal (thio)ester can be synthesized using solid phase synthesis in high yield and purity without racemization. An additional advantage of the use of (thio)esters of the carboxyamidomethyl type wherein $R_1$ represents a hydrogen atom and $R_2$ represents an amino acid or peptide residue with a C-terminal carboxylic acid functionality, optionally protected on the side-chain functionality of the amino acid or on one or more of the side-chain functionalities of the amino acids is, that their activated C-terminal ester or thioester group can be synthesized using the cheap and industrially available 2-chlorotritylchloride resin.

The activated C-terminal (thio)ester group of the peptide C-terminal (thio)ester can also be synthesized by solution phase synthesis or fermentation using a microorganism. A reliable method to obtain peptide (thio)esters using fermentation is via so-called intein expression (see for instance E. K. Lee, Journal of Chemical Technology and Biotechnology, 2010, 9, 11-18). Different intein expression systems kits are commercially available (for instance the IMPACT™ kit). Other methods for the fermentative production of peptide (thio)esters are known in the art.

The C-terminal amino acid of the peptide C-terminal (thio)ester and the other amino acids of the peptide C-terminal (thio)ester may in principle be any amino acid, proteinogenic or non-proteinogenic. If the amino acid sequence of the C-terminal part of the peptide C-terminal (thio)ester is poorly recognized by or inaccessible to the coupling enzyme due to the amino acid preference of the coupling enzyme and/or due to the secondary or tertiary structure of the peptide, the primary structure (amino acid sequence) may be elongated at the C-terminus. Essentially the C-terminus of the peptide C-terminal (thio)ester is elongated with a number of amino acids to ensure good recognition by the enzyme and accessibility into the enzyme for the enzymatic coupling reaction. The skilled person will know how to elongate the peptide C-terminal (thio)ester on the basis of the information disclosed herein and common general knowledge. Usually the number of amino acids for elongation is in the range of 1-10, although in principle it can be higher. Good results have been obtained by elongation of the peptide C-terminal (thio)ester with 4 amino acid residues, e.g. -Phe-Ser-Lys-Leu-(thio)ester.

In particular the (optionally N-terminal protected) peptide C-terminal (thio)ester may be represented by a compound of Formula I.

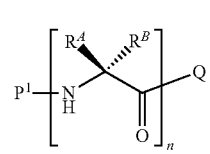

Formula I

Herein Q represents an OR or SR moiety. R may represent a (substituted or unsubstituted) alkyl or a (substituted or unsubstituted) aryl group.

Herein $P^1$ stands for a hydrogen or an N-terminal protecting group. Suitable N-terminal protecting groups are those N-protecting groups which can be used for the synthesis of peptides. Such groups are known to the person skilled in the art. Examples of suitable N-protecting groups include carbamate or acyl type protecting groups, for instance 'Cbz' (benzyloxycarbonyl), 'Boc' (tert-butyloxycarbonyl), 'For' (formyl), 'Fmoc' (9-fluorenylmethoxycarbonyl), 'PhAc' (phenacetyl) and 'Ac' (acetyl). The groups For, PhAc and Ac may be introduced and cleaved enzymatically using the enzymes Peptide Deformylase, PenG acylase or Acylase, respectively. Chemical cleavage methods are generally known in the art.

Herein, n is an integer of at least 2. n May in particular be at least 3, at least 4, at least 5, at least 6, at least 7 at least 8, at least 9 or at least 10. In principle there is no upper limit to n, but in general n may in particular be 10.000 or less, 1000 or less, 500 or less, e.g. 100 or less, 50 or less or 40 or less.

Herein, each $R^A$ and each $R^B$ independently represent a hydrogen atom or an organic moiety, preferably an amino acid side-chain. Thus, it is not required that $R^A$ is the same in all n amino acid units. Similarly, it is not required that $R^B$ is the same in all n amino acid units. Optionally, one or more of the side-chain functionalities may contain a protecting group.

The amino acid units of the peptide nucleophile may in principle be selected from any amino acid, proteinogenic or non-proteinogenic.

In particular, the peptide nucleophile may be represented by a compound of Formula II.

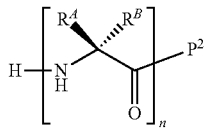

Formula II

The term 'C-terminal protection' is used herein to indicate that a C-terminal carboxylic group of a peptide is provided with a protective group, generally substantially protecting the carboxylic group from being coupled to an N-terminal amine group of another peptide or of the same peptide molecule.

Herein, n, $R^A$ and $R^B$ are as defined above.

Herein $P^2$ represents an amine moiety or an OR moiety.

In case $P^2$ represents an amine moiety, the amine moiety may be represented by the formula $NR_3R_4$, in which $R_3$ and $R_4$ may each individually represent any (substituted or unsubstituted) alkyl or (substituted or unsubstituted) aryl group. In particular, one out of $R_3$ and $R_4$ is a hydrogen atom and the other a (substituted or unsubstituted) alkyl group. Good results have particularly been obtained with $R_3$ and $R_4$ both being a hydrogen atom.

In case $P^2$ represents an OR moiety, R may represent a C-terminal protective group or a cation, for instance a monovalent cation, such as a tri- or tetrasubstituted ammonium ion or an alkaline metal cation or an H.

In case R is a C-terminal protective group this may in particular be an optionally substituted alkyl group. Preferably it is a t-alkyl group, although in principle it also may be any other protective ester as known to a man skilled in the art. The t-alkyl may in principle be any protective tertiary alkyl group. Preferably the t-alkyl is selected from the group of t-butyl (2-methyl-2-propyl), t-pentyl (2-methyl-2-butyl) and t-hexyl (2,3-dimethyl-2-butyl).

In an embodiment, the peptide nucleophile is C-terminal protected. In another embodiment it is not C-terminal protected.

In particular, good results have been achieved with peptide nucleophiles without protected side-chain functionalities.

In an embodiment, one or more side-chain functionalities (in particular one or more hydroxyl groups, carboxyl groups or amine groups) of the peptide nucleophile are provided with a protecting group. Suitable protecting groups are known to the person skilled in the art. Carboxylic acid groups can for instance be protected with a cyclohexyl, benzyl or allyl group; amine functionalities can for instance be protected with an allyloxycarbonyl group or a trifluoroacetyl group.

The peptide nucleophile may be synthesized using methods known in the art, such as solid-phase synthesis, solution phase synthesis or by fermentation using a microorganism. The N-terminal amino acid of the peptide nucleophile and the other amino acids of the peptide nucleophile may in principle be any amino acid, proteinogenic or non-proteinogenic. If the amino acid sequence of the N-terminal part of the peptide nucleophile is poorly recognized by or inaccessible to the coupling enzyme due to the amino acid preference of the coupling enzyme or due to the secondary or tertiary structure of the peptide nucleophile, the primary structure (amino acid sequence) may be elongated at the N-terminus. Essentially the N-terminus of the peptide nucleophile is elongated with a number of amino acids to ensure good recognition by and accessibility to the coupling enzyme for the enzymatic coupling reaction. The skilled person will know how to elongate the peptide nucleophile on the basis of the information disclosed herein and common general knowledge. Usually the number of amino acids for elongation is in the range of 1-10, although in principle it can be higher. Good result have been obtained by elongation of the peptide nucleophile with 3 amino acid residues, e.g. H-Ser-Tyr-Arg.

An enzyme according to the invention is a subtilisin BPN' variant or homologue thereof.

In particular, the invention provides an isolated enzyme (isolated from the organism wherein it has been expressed (typically a recombinant organism), if it has been produced in an organism or from the reaction medium in which it has been synthesized).

In particular, an enzyme of the invention is considered isolated for the purpose of the invention either in the crude form or substantially purified by any suitable technique such as, for example, the single-step purification method disclosed in Smith and Johnson, Gene 67:31-40 (1988).

An enzyme of the present invention can be provided in at least substantially pure form (e.g. more than 75 wt. %, more than 80 wt. %) or in a mixture with one or more other components, e.g. in the form of a stock solution, in particular in an aqueous buffer solution.

The present disclosure provides various examples of enzymes of the invention, which are in particular considered subtilisin BPN' variants. As already described above, an enzyme of the invention should comprise at least a deletion of the amino acids corresponding to positions 75-83 in subtilisin BPN';

a mutation at the amino acid position corresponding to S221, the mutation being S221C or S221 selenocysteine, preferably S221C, in subtilisin BPN';

at least one further mutation selected from the group consisting of amino acid positions corresponding to F189W, F189Y, S33D, S33T, N218D, N218T, N218E, N62D, N62S, N62W, and N62Y in subtilisin BPN'.

A mutation corresponding to F189W or F189Y is highly preferred for a broad(er) substrate scope, in particular with respect to the amino acids in the P2' and P1' positions of the peptide nucleophile, whilst a satisfactory S/H ratio is maintained or the S/H ratio is improved. Of these two mutations, F189W is particularly preferred. Advantageously, an enzyme having a mutation corresponding to F189W or F189Y, in particular a mutation corresponding to F189W, also has a mutation corresponding to N218D. Advantageously, an enzyme having a mutation corresponding to N218D and a mutation corresponding to F189W or F189Y further has at least one mutation corresponding to M222P, Y217H or P225N, preferably each of these.

A mutation corresponding to N218D, N218T or N218E is preferred for a broad(er) substrate scope with respect to the amino acids in the P2' position and/or P1' position of the peptide nucleophile, whilst a satisfactory S/H ratio is maintained or the S/H ratio is improved. Of these mutations N218D is particularly preferred.

A mutation corresponding to S33D or S33T is highly preferred for a broad(er) substrate scope, in particular with respect to the amino acids in the P2 position of the peptide C-terminal (thio)ester, and/or in the P1' position and/or in the P2' position of the peptide nucleophile, whilst a satisfactory S/H ratio is maintained or the S/H ratio is improved. Of these two mutations, S33D is particularly preferred.

A mutation corresponding to N62D, N62S, N62W, N62Y is preferred for a broad(er) substrate scope, in particular with respect to the amino acid in the P2 position of the peptide C-terminal (thio)ester, and/or in the P1' and/or P2' positions of the peptide nucleophile, whilst a satisfactory S/H ratio is maintained, or the S/H ratio is improved. Of these mutations, N62D is particularly preferred.

In particular, good results have been achieved with an enzyme comprising a mutation in the S2 pocket of the enzyme at an amino acid position corresponding to S33D and further comprising a mutation in the S2' pocket corresponding to N62S. Further, in particular good results have been achieved with an enzyme comprising a mutation in the S2 pocket of the enzyme at an amino acid position corresponding to S33T and further comprising a mutation in the S2' pocket corresponding to N62W or N62V. Enzymes with such a combination of the specific amino acid at the position corresponding to S33 and the specific amino acid at the position corresponding to N62 have been found to have a distinct substrate specificity over the comparative enzyme with either the specific amino acid at the S33 position (D or T) or the specific amino acid at the N62 position (W or V). Moreover the combination has been found to offer a synergistic effect in terms of S/H ratio and enzymatic coupling activity. Preferably, for a synergistic effect and/or providing a distinct substrate specificity, said enzyme having the mutations corresponding to S33D+N62S or to S33T+N62W or to S33T+N62V further comprises the mutations corresponding to M222P, Y217H and I107V, more preferably the mutations corresponding to M222P, Y217H, P225N, F189W, N218D and I107V.

In a particularly preferred embodiment, the subtilisin BPN' variant or homologue thereof comprises at least 2, even more preferably at least 3 and most preferably 4 mutations at positions selected from the group of positions corresponding to F189, N218, S33 and N62. Herein, most preferably, the mutation at the position corresponding to F189 corresponds to F189Y or F189W, the mutation at the position corresponding to N218 corresponds to N218D, N218T or N218E, the mutation at the position corresponding to S33 corresponds to S33D or S33T and the mutation at the position corresponding to N62 corresponds to N62D, N62S, N62W or N62Y.

An enzyme of the invention may have further mutations compared to subtilisin BPN', provided that it has enzymatic fragment condensation activity (coupling activity) or cyclisation activity in the preparation of a peptide, in particular one or more further mutations as described elsewhere herein.

Alternatives to subtilisin BPN', as template enzymes from which an enzyme according to the invention, in particular a homologue of a subtilisin BPN' variant of the invention, can be derived by mutagenesis are other subtilisins, in particular subtilisins having at least 50% homology with subtilisin BPN'.

Sequences of suitable subtilisins can be retrieved from the UNIPROT sequence database (www.uniprot.org/), as available on 11 Aug. 2014, by BLASTing the database with subtilisin BPN' (SEQ ID 2) as a query. However sequence retrieval is not limited to UNIPROT nor to the date. The skilled person in the art knows how to query alternative sequence depositories or to collect additional homologue sequences by sequencing (see for example *Zooming in on metagenomics: molecular microdiversity of Subtilisin Carlsberg in soil*. Gabor E, Niehaus F, Aehle W, Eck J. J Mol Biol. 2012 Apr. 20; 418(1-2):16-20). In particular, the invention further relates to variants, having at least said deletions of the amino acids corresponding to L75 till and including G83 of subtilisin BPN', cysteine or selenocystein at a position corresponding to position 221 in subtilisin BPN' and at least one of said further mutations in present claim 1.

The sequence of subtilisin BPN' is given in SEQ ID NO: 2 (mature form). The gene encoding for subtilisin BPN' amino acids −107 to 275 is given in SEQ ID NO: 1. The subtilisin BPN' variant or homologue can be based on the enzymes according to WO 2016/056913, with the proviso that it has the above mentioned mutations.

SEQ ID NO: 3 shows a subtilisin BPN' variant according to the invention with deletion of $Ca^{2+}$ binding loop, the S221 mutation (denoted as S221X), the positions S33, N62, E156, G166, F189, N218 (all marked as X, denoting any proteinogenic amino acid, provided at least one is a mutation, and the P225 position marked as X (any proteinogenic amino acid, preferably a mutation as defined elsewhere herein). Further preferred enzymes may comprise one or more additional mutations, in particular one or more further mutations as identified elsewhere herein or in WO 2016/056913, incorporated herein by reference.

The mutation at the amino acid position corresponding to S221 of an enzyme according to the invention preferably is S221C.

The mutation at the amino acid position corresponding to P225 is usually advantageous for the S/H ratio for a coupling or cyclisation reaction of interest. The mutation is usually selected from the group of P225N, P225D, P225S, P225C, P225G, P225A, P225T, P225V, P225I, P225L, P225H, P225Q, preferably from the group of P225N, P225D, P225S, P225C and P225G, more preferably P225N or P225D.

For a good enzyme stability, the subtilisin BPN' variant or homologue thereof preferably comprises one or more mutations selected from the group of mutations at an amino acid position corresponding to Q2, S3, P5, S9, I31, K43, M50, A73, E156, G166, G169, S188, Q206, N212, N218, T254 and Q271 of SEQ ID NO 2. As described elsewhere herein, a specific mutation at N218 is further advantageous with respect to S/H ratio and/or substrate scope. In an embodiment the position corresponding to N218 is not mutated, whilst enzyme stability is at least substantially maintained, compared to an enzyme wherein this position has been mutated.

Preferably said one or more mutations (preferred for a good enzyme stability) are selected from the group Q2K, S3C, P5S, S9A, I31L, K43N, M50F, A73L, E156S, G166S, G169A, S188P, Q206C, N212G, T254A and Q271E. In a particularly preferred embodiment, the subtilisin BPN' variant or homologue thereof comprises at least six, preferably at least eight, more in particular at least 12 of said mutations selected from the group of Q2K, S3C, P5S, S9A, I31L, K43N, M50F, A73L, E156S, G166S, G169A, S188P, Q206C, N212G, T254A and Q271E.

In a preferred embodiment the subtilisin BPN' variant or homologue thereof comprises one or more mutations at the amino acid position corresponding to G100, S125, L126, G127, P129, and N155, of SEQ ID NO 2.

In a specific embodiment, the subtilisin BPN' variant or homologue thereof comprises mutations at the amino acid positions corresponding to M222 and Y217, wherein the mutations are:
M222P and Y217H;
M222P and Y217G;
M222G and Y217F; or
M222G and Y217G;

In a further embodiment, the subilisin BPN' or homologue thereof, comprises at least one mutation selected from the group of mutations at an amino acid position corresponding to Y104, I107, S101, G102, 128, L135 and P168 of SEQ ID NO 2, which mutation or mutations may in particular be selected from the group of Y104F, Y104S, I107V, I107A, L135N, L135S, L135D or L135A.

In the method of the invention the enzymatic coupling reaction respectively the enzymatic cyclisation reaction are typically performed in a fluid comprising water. Preferably the reaction is performed in a buffered fluid. The water content usually is 10-100 vol %, based on total liquids, preferably 20 vol. % or more, preferably 40 vol. % or more, in particular 50 vol. % or more, in particular 60 vol. % or more. In particular good results have been achieved in a reaction medium, comprising 70-100 vol % water, more in particular 90-100 vol. %, 95-100 vol. % or 98-100 vol. % water. The term 'aqueous' is used for media at least substantially consisting of water.

In principle, any buffer is suitable. Good buffers are known to a person skilled in the art. See for instance David Sheehan in Physical Biochemistry, 2nd Ed. Wiley-VCH Verlag GmbH, Weinheim 2009; www.sigmaaldrich.com/life-science/core-bioreagents/biological-buffers/learning-center/buffer-calculator.html.

The pH of the buffer for a peptide fragment condensation may be at least 5, in particular at least 6, preferably at least 7. A desired pH is usually less than 11, in particular less than 10, even more preferably less than 9. Usually the optimal pH for the enzymatic fragment condensations is between 7 and 9. For cyclisation reactions the optimal pH can be different. The pH for the cyclisation reaction may be at least 3, in particular at least 4, preferably at least 5. A desired pH is usually less than 11, in particular less than 10, preferably less than 9. Usually the optimal pH for the enzymatic cyclisation reactions is between 5 and 9.

Due to the high S/H ratio, a large excess of the peptide C-terminal ester or thioester or of the peptide nucleophile is generally not needed to reach a high yield in the condensation reaction. Usually the ratio of (a) the peptide C-terminal ester or thioester to (b) the peptide nucleophile is between 1:5 and 5:1, preferably in the range of 1:3 to 3:1, more preferably in the range of 1.0:2.5 to 2.5:1.0, in particular in the range of 1:2 to 2:1, more in particular in the range of 1:1.5 to 1.5:1. An about stoichiometric ratio has been found particularly effective.

In the method of the invention, it may be advantageous to add additives to the fluid wherein the reaction is carried out to improve the solubility of the peptide fragments or to improve the reaction yield. Such additives may be a salt or an organic molecule, for instance guanidinium hydrochloride, urea, sodium dodecasulphate or Tween.

The reaction may be carried out in a fully aqueous liquid or in a mixture of water and a water miscable co-solvent such as N,N-dimethylformamide (DMF), N-methyl-pyrrolidinone (NMP), N,N-dimethylacetamide (DMA), dimethylsulphoxide (DMSO), acetonitrile, an ether, such as tetrahydrofuran (THF), 2-methyl-tetrahydrofuran (Me-THF) or 1,2-dimethoxyethane, or a (halogenated) alcohol, such as methanol, ethanol, isopropanol, tert-butanol, 2,2,2-trifluoroethanol (TFE), 1,1,1,3,3,3-hexafluoroisopropanol, or a mixture of these organic solvents. Depending on the stability of the subtilisin BPN' variant and the solubility of the peptide substrates, the amount of co-solvent is preferably below 70 vol %, more preferably below 60 vol %, even more preferably below 50 vol %, and most preferably below 40%.

In principle the temperature during the enzymatic fragment condensations or cyclisations is not critical, as long as a temperature is chosen at which the enzyme to be used shows sufficient activity and stability. Such a temperature can be routinely determined. Generally, the temperature may be at least −10° C., in particular at least 0° C. or at least 10° C. Generally, the temperature may be 70° C. or less, in particular 60° C. or less or 50° C. or less. Optimal temperature conditions can easily be identified for a specific enzyme for a specific enzymatic fragment condensation or cyclisation by a person skilled in the art through routine experimentation based on common general knowledge and the information disclosed herein. In general, the temperature advantageously is in the range of 20-50° C.

The enzymes of the present invention are generally produced by recombinant methods, in particular by expression of a subtilisin BPN' DNA which has been mutated such that upon expression it results in a subtilisin BPN' variant of the invention which is enzymatically active.

Accordingly, the invention further relates to a recombinant method for preparing the enzyme according to the invention, said method comprising:
a) providing a recombinant host cell functionally expressing a gene encoding the enzyme, e.g. bacterial cells such as *E. coli* or *Bacillus;*
b) culturing said host cell under conditions which provide for the expression of the enzymatically active enzyme; and
c) recovering the expressed enzyme from said microbial host.

The invention further relates to a recombinant polynucleotide comprising a sequence which encodes for an enzyme according to the invention.

The invention further relates to a host cell, comprising a polynucleotide according to the invention, which polynucleotide is capable of expressing the enzyme.

The use of an enzyme according to the invention as a catalyst to the invention extends beyond the cyclisation of a peptide respectively the coupling of a peptide C-terminal ester or thioester to a peptide nucleophile, such as described above.

The enzyme can be used in the formation of an amide bond, other than a peptide bond, although the use in catalysing the formation of a peptide bond is a particularly preferred use of the enzyme.

The invention will now be illustrated by the following examples, without being limited thereto.

EXAMPLES

Production of Enzymes (for Use) According to the Invention
Mutagenesis, Cloning and Expression The enzyme denoted as BS149-DM corresponds to SEQ ID NO:2 with deletion of the amino acids corresponding to positions 75-83 and including the additional mutations Q2K, S3C, P5S, S9A, I31L, K43N, M50F, A73L, E156S, G166S, G169A, S188P, Q206C, N212G, Y217L, N218S, S221C, P225A, T254A and Q271E. The gene coding for BS149-DM with a His-tag was cloned into a pUB-110 based E. coli-B. subtilis shuttle vector (i.e. pBS42 or pBES (see also WO2016/056913). The corresponding amino acid sequence is numbered according to the subtilisin BPN' numbering scheme. Amino acids −107 to −1 comprise the signal sequence, the pre sequence and a pro sequence which are cleaved off upon full maturation. Amino acids 1-275 comprise the mature enzyme which exhibits the full catalytic activity. In order to enable a fast and efficient purification after amino acid 275 a C-terminal His-tag is attached. As a consequence of the removal of the calcium binding site BS149-DM contains a deletion of 9 amino acids compared to subtilisin BPN' comprising the amino acids corresponding to L75, N76, N77, S78, I79, G80, V81, L82 and G83 in subtilisin BPN'. In order to maintain the subtilisin BPN' numbering for BS149-DM the numbering jumps from 74 to 83. In the shuttle vector, the expression of the gene is under the control of aprE promoter. The resulting plasmid pBES-BS149DMHIS was propagated in E. coli TOP10 and transformed into B. subtilis GX4935 (trpC2 metB10 lys-3ΔnprEΔaprE). Using pBES-BS149DMHIS as the template, mutagenesis was carried out by the Quikchange method (Agilent). Alternatively other methods for site directed mutagenesis known in the art may be used (Sambrook et al., 1989.). Alternatively, DNA was synthesized by GenScript, USA and incorporated into the respective shuttle vector.

Production and Purification of Synthetic Subtilisin BPN' Variants which Carry a His-Tag:

A single microbial colony of B. subtilis containing a plasmid with the subtilisin variant gene of interest was inoculated in 5 mL LB with kanamycin (10 μg/mL) at 37° C. in a shaking incubator. To the 30 mL Terrific Broth supplemented with antibiotic (kanamycin 10 μg/mL) and amino acids (100 mg/L Trp, 100 mg/L Met and 100 mg/L Lys) 0.6 mL of the overnight culture was added. The cells were grown 48h at 37° C. in a shaking incubator (200 rpm). The cells were harvested by centrifugation (30 min, 4,000 rpm, 4° C.). The medium (30 mL) was decanted and concentrated on Amicon-centrifugal unit (15 ml, 10 kDa MW cut-off) in two centrifugation steps (15 min, 4000 rpm, 4° C.). The concentrated medium (0.5 ml) was then exchanged for buffer A (25 mM Tricine, pH 7.5, 0.5M NaCl) in three washing/concentrating steps (14 ml buffer A, 10 min, 4,000 rpm, 4° C.). For His-tag purification Talon resin (2.5 ml, Clonetech) was added to a plastic column cartridge. The resin was washed with 5 mL MilliQ water and equilibrated with 5 mL of buffer A. The crude enzyme was loaded on the column and incubated overnight at orbital shaker at 4° C. After incubation the resin was washed with 25 mL buffer A. The enzyme was eluted with 15 mL buffer B (25 mM Tricine, pH 7.5, 0.5M NaCl, 0.5M imidazole). The elute was concentrated on a Amicon-centrifugal unit (15 ml, 10 kDa MW cut-off) by centrifugation (30 min, 4000 rpm, 4° C.) and the buffer was exchanged to 25 mM Tricine, pH 7.5 in three washing/concentrating steps (15 ml buffer, 10 min, 4,000 rpm, 4° C.).

The purity and enzyme concentration was determined as described above Purity was more than 90%, The obtained aqueous solution (25 mM Tricine, pH 7.5) containing about 0.1-2 mg/ml of the obtained enzyme was used as such for the oligopeptide fragment condensations and cyclisations.

REFERENCES

Abrahmsén, L, J Tom, J Burnier, K A Butcher, A Kossiakoff, and J A Wells. 1991. "Engineering Subtilisin and Its Substrates for Efficient Ligation of Peptide Bonds in Aqueous Solution." Biochemistry 30 (17) (April 30): 4151-9. www.ncbi.nlm.nih.gov/pubmed/2021606.

Fahnestock S R, Fisher K E: Expression of the staphylococcal protein A gene in Bacillus subtilis by gene fusions utilizing the promoter from a Bacillus amyloliquefaciens alpha-amylase gene. J Bacteriol. 1986 March; 165(3): 796-804

Kawamura, Fujio, and Roy H. Doi. Construction of a Bacillus subtilis double mutant deficient in extracellular alkaline and neutral proteases. J Bacteriol. 1984 October; 160(1):442-4

Ruan, Biao, Viktoriya London, Kathryn E Fisher, D Travis Gallagher, and Philip N Bryan. Engineering substrate preference in subtilisin: structural and kinetic analysis of a specificity mutant. Biochemistry. 2008 Jun. 24; 47(25): 6628-36.

Sambrook J, Fritsch E F, Maniatis T. 1989. Molecular Cloning: A Laboratory Manual. 2nd edition. Cold Spring Harbor Laboratory Press, Cold Spring Harbor, N.Y.

Wells, James A, Eugenio Ferrari, Dennis J Henner, David A Estell, and Ellson Y Chen.

Cloning, sequencing, and secretion of Bacillus amyloliquefaciens subtilisin in Bacillus subtilis. Nucleic Acids Res. 1983 Nov. 25; 11(22):7911-25.

Enzymatic Fragment Condensation and Cyclisation Examples
Materials and Methods

Unless stated otherwise, chemicals were obtained from commercial sources and used without further purification. Analytical HPLC was performed on an HP1090 Liquid Chromatograph, using a reversed-phase column (Phenomenex, C18, 5 μm particle size, 150×4.6 mm) at 40° C. UV detection was performed at 220 nm using a UV-VIS 204 Linear spectrometer. The gradient program was: 0-25 min linear gradient ramp from 5% to 98% eluent B and from 25.1-30 min 5% eluent B (eluent A: 0.5 mL/L methane sulfonic acid (MSA) in $H_2O$, eluent B 0.5 mL/L MSA in acetonitrile). The flow was 1 mL/min from 0-25.1 min and 2 mL/min from 25.2-29.8 min, then back to 1 mL/min until stop at 30 min. Injection volumes were 20 μL. Preparative HPLC was performed on a Varian PrepStar system using a stationary-phase column (Pursuit XRs, C18, 10 μm particle size, 500×41.4 mm). LC-MS was performed on an Agilent 1200 series Liquid Chromatograph, using a reversed-phase column (Phenomenex, C18, 5 μm particle size, 150×4.6 mm) at 40° C. UV detection and gradient program were as described for analytical HPLC. The molecular weights were determined using an Agilent 6130 quadrupole LC/MS system.

Protocol 1: Oligopeptide-OCam-Leu-OH Esters were Synthesized as Described Below:

1 gram of Fmoc-Leu-Wang resin (with a loading of 0.72 mmol/gram) was washed with DCM (2×2 min, 10 mL) and DMF (2×2 min, 10 mL) and Fmoc-deprotected using piperidine/DMF (1/4, v/v, 2×8 min, 10 mL). After washing with DMF (2×2 min, 10 mL), DCM (2×2 min, 10 mL) and DMF (2×2 min, 10 mL), iodoacetic acid (4 equiv.) was coupled to the resin using DCC (4 equiv.) and HOAt (4 equiv.) in DCM (45 min, 10 mL). After washing with DMF (2×2 min, 10 mL), DCM (2×2 min, 10 mL) and THF (2×2 min, 10 mL), the resin was loaded with an Fmoc-protected amino acid using 4 equiv. Fmoc-Xxx-OH and 10 equiv. DiPEA in DMF/THF (1/1, v/v, 10 mL) at 50° C. for 20h. Here and in other parts of this disclosure 'Xxx' stands for one amino acid (variable as indicated in the Figures belonging to the examples below).

After washing with DMF (2×2 min, 10 mL), DCM (2×2 min, 10 mL) and DMF (2×2 min, 10 mL), standard SPPS protocols were followed to elongate the peptide (Weng C. Chan and Peter White, OUP Oxford, 2000). Cleavage from the resin and side-chain deprotection was performed using a mixture of trifluoroacetic acid (TFA), triisopropylsilane (TIS) and water (95/2.5/2.5, v/v/v, 15 mL) for 120 min. The crude peptide was precipitated using methyl tert-butyl ether (MTBE)/n-heptanes (1/1, v/v, 50 mL). The precipitated peptide was collected by centrifugation and washed twice with MTBE/n-heptanes (1/1, v/v, 50 mL) followed by lyophilization from acetonitrile/water (1/1, v/v, 50 mL).

Protocol 2: Oligopeptide C-Terminal Amide Nucleophiles were Synthesized as Described Below:

1 gram of Rink resin (4-((2,4-dimethoxyphenyl)(Fmoc-amino)methyl)-phenoxyalkyl linker, with a loading of 0.64 mmol/gram) was washed with DCM (2×2 min, 10 mL) and DMF (2×2 min, 10 mL) and Fmoc-deprotected using piperidine/DMF (1/4, v/v, 2×8 min, 10 mL). Standard SPPS protocols were followed to elongate the peptide (Weng C. Chan and Peter White, OUP Oxford, 2000). Cleavage from the resin and side-chain deprotection was performed using a mixture of TFA/TIS/water (95/2.5/2.5, v/v/v, 15 mL) for 120 min. The crude peptide was precipitated using MTBE/n-heptanes (1/1, v/v, 50 mL). The precipitated peptide was collected by centrifugation and washed twice with MTBE/n-heptanes (1/1, v/v, 50 mL) followed by lyophilization from acetonitrile/water (1/1, v/v, 50 mL).

Protocol 3: N-Acetyl-Protected Oligopeptide Activated Esters were Synthesized as Described Below:

After SPPS of the desired sequence according to one of the protocols 1, the resin bound peptide was Fmoc-deprotected using piperidine/DMF (1/4, v/v, 2×8 min, 10 mL). The resin was washed with DMF (2×2 min, 10 mL), DCM (2×2 min, 10 mL) and DMF (2×2 min, 10 mL) and the peptide N-terminal amine function was acetylated using a mixture of $Ac_2O$ (10 vol %), DiPEA (5 vol %), HOBt (0.2 wt %) in DMF (2×10 min, 10 mL). The resin was washed with DMF (3×2 min, 10 mL) and DCM (3×2 min, 10 mL). Cleavage from the resin and side-chain deprotection was performed using a mixture of TFA/TIS/water (95/2.5/2.5, v/v/v, 15 mL) for 120 min. The crude peptide was precipitated using MTBE/n-heptanes (1/1, v/v, 50 mL). The precipitated peptide was collected by centrifugation and washed twice with MTBE/n-heptanes (1/1, v/v, 50 mL) followed by lyophilization from acetonitrile/water (1/1, v/v, 50 mL).

Coupling Examples

Note: the enzyme denoted as BS149-DM corresponds to SEQ ID NO:2 with deletion of the amino acids corresponding to positions 75-83 and including the additional mutations Q2K, S3C, P5S, S9A, I31L, K43N, M50F, A73L, E156S, G166S, G169A, S188P, Q206C, N212G, Y217L, N218S, S221C, P225A, T254A and Q271E. All other enzymes used in the Examples 1-5 have all these mutations of BS149-DM, plus the additional mutations as mentioned in the Examples. BS149-DM and the enzymes with further mutations were produced using the technology described above.

Example 1: Mapping of the P1' and P2' Pocket Substrate Specificity of Different Enzyme Variants with a Mutation in the P2' Pocket To determine P1' and P2' pocket substrate specificity of the different mutants, the following two standard reactions were performed. 800 μL of phosphate buffer (100 mM, pH 8.0) was added to a mixture of 100 μL tripeptide C-terminal amide stock solution (0.01 mmol H-Xxx-Leu-Arg-$NH_2$.2TFA for the P1' pocket and H-Ala-Xxx-Arg-$NH_2$.2TFA for the P2' pocket in 300 μL water) and 100 μL pentapeptide C-terminal Cam-ester stock solution (0.01 mmol Ac-Asp-Phe-Ser-Lys-Leu-OCam.TFA in 1200 μL water). To this mixture 5.5 μg enzyme was added and the reaction mixture was shaken (150 rpm) at room temperature. After 30 min a 550 μL aliquot of the reaction mixture was withdrawn and quenched with 500 μL MSA/water (1/99, v/v) and analyzed by LC-MS. The coupling product, the hydrolysed pentapeptide C-terminal Cam-ester and the remaining pentapeptide C-terminal Cam-ester peaks were integrated. The area % product is defined as the amount of product divided by the total of the amount of product, hydrolysed pentapeptide C-terminal Cam-ester and remaining pentapeptide C-terminal Cam-ester, within the specified reaction time.

Figure 1B:
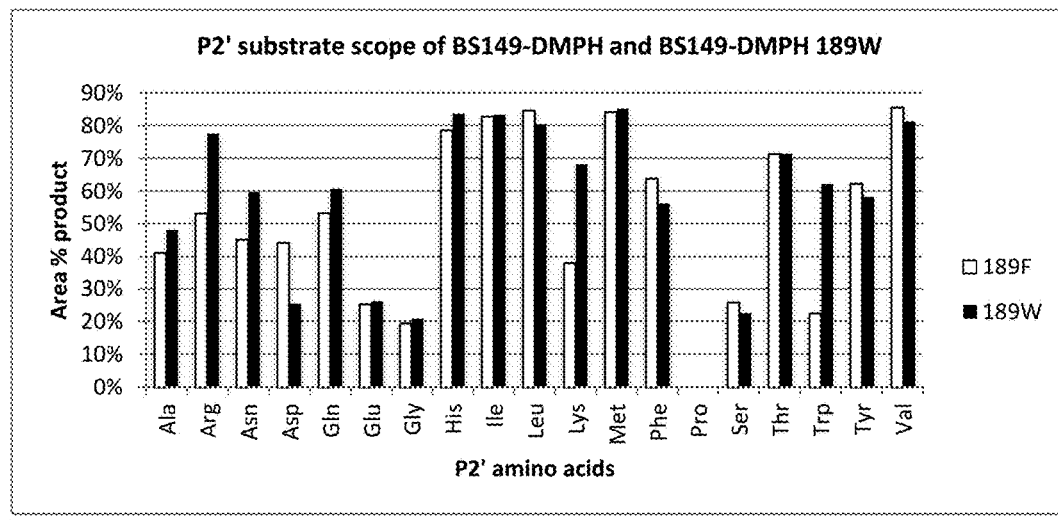

The P2' substrate scope for BS149-DM+222G+217F (BS149-DMGF) and BS149-DM+222G+217F+189W/Y (BS149-DMGF+189W/Y) and BS149-DM+222P+217H (BS149-DMPH) and BS149-DM+222P+217H+189W (BS149-DMPH+189W) are shown in FIGS. 1A and 1B, respectively.

The P2' and P1' substrate scope for BS149-DM+222P+217H+225N+107V (BS149-DMPHNV) and BS149-DM+222P+217H+225N+107V+F189W (BS149-DMPHNV+189W) are shown in FIGS. 1 C and 1 D, respectively.

Figure 2:
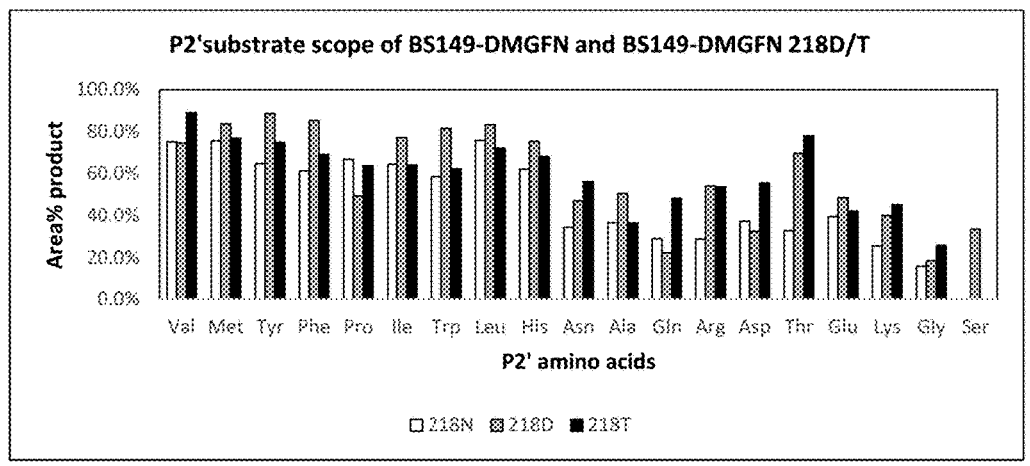
FIG. 2: The P2' substrate scope for BS149-DMGFN and BS149-DMGFN+N218D/T

The P2' substrate scope for BS149-DM+222G+217F+225N+218N (BS149-DMGFN) and BS149-DM+222G+217F+225N+N218D/T (BS149-DMGFN+N218D/T) are shown in FIG. 2.

Conclusions

Figure 1C:
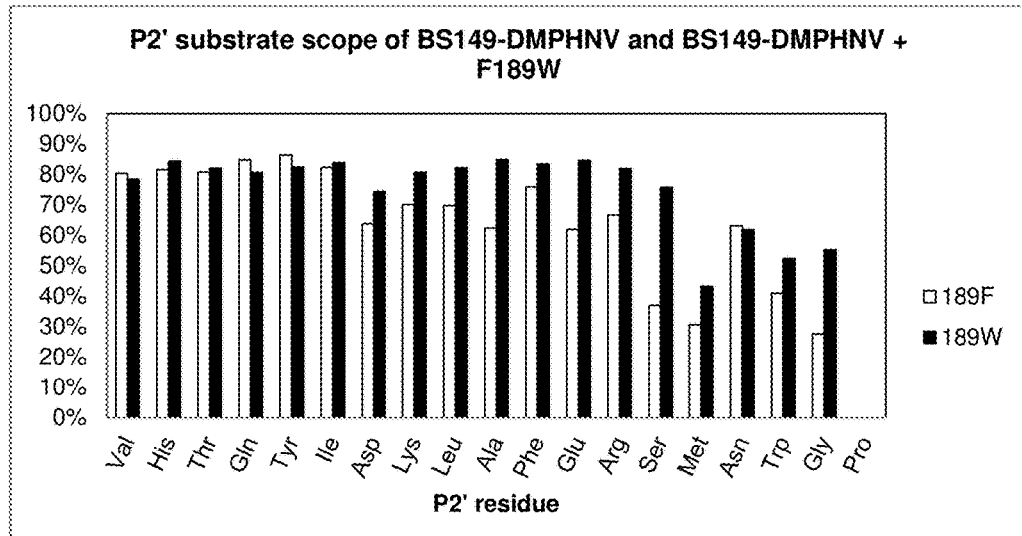

The mutations F189W and F189Y have a positive effect with regards to the P2' substrate scope and coupling efficiency (FIG. 1A-1C).

Figure 1D:
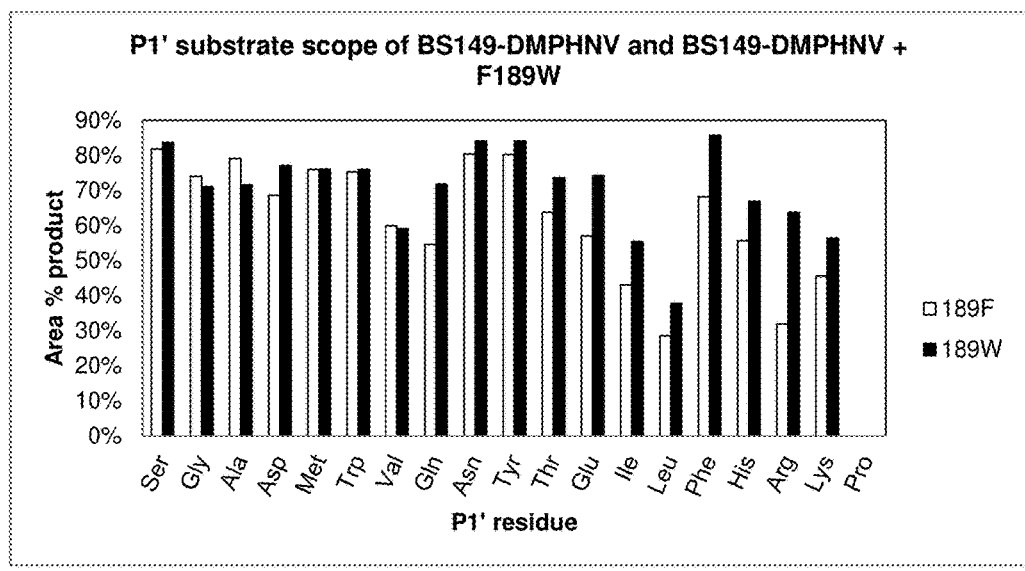

The P2' mutation F189W has a clearly positive effect with regards to the P1' substrate scope and coupling efficiency (FIG. 1D).

The mutations N218D and N218T have a positive effect with regards to the P2' substrate scope and coupling efficiency (FIG. 2).

Example 2: Mapping the P2' Pocket Substrate Specificity of Different Enzyme Variants with a Mutation in the P2' Pocket To determine P2' pocket substrate specificity of the different mutants, the following reactions were performed. First, the substrate premix (20 µl) was prepared from respective stock solutions in water with final concentrations of 10 mM pentapeptide Cam-ester Ac-Asp-Phe-Ser-Lys-Leu-OCam.TFA. and 15 mM of C-terminal amide H-Ala-Xxx-Lys-Lys(DNP)Lys-NH$_2$.2TFA (with DNP being a dinitrophenyl protecting group). To this mixture 20 µl of enzyme solution in 1M Tricine buffer pH 8.5 supplemented with TCEP (tris-(2-carboxyethyl)phosphine hydrochloride, 0.1 mg/ml) was added. In total 0.4 µg enzyme was added per well and the reaction mixture was shaken (150 rpm) at room temperature. After 30 min a 10 µL aliquot of the reaction mixture was withdrawn and quenched with 150 µL MSA/water (2/98, v/v), diluted with 350 µl water and analyzed by LC-MS. The coupling product, the hydrolysed pentapeptide C-terminal Cam-ester and the remaining pentapeptide C-terminal Cam-ester peaks were integrated. The area % product is defined as the amount of product divided by the total of the amount of product, hydrolyzed pentapeptide C-terminal Cam-ester and remaining pentapeptide C-terminal Cam-ester, within the specified reaction time. Data were normalized to 100% with regard to the highest conversion obtained in the screening.

Figure 5:
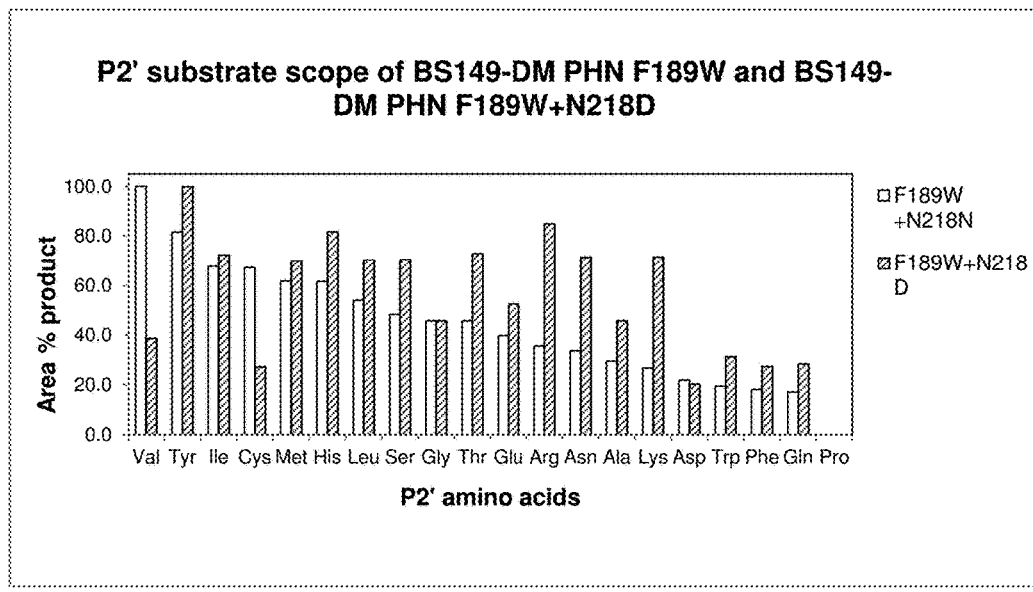
FIG. 5: P2' substrate scope for BS149-DM PHN F189W and BS149-DM PHN F189W+N218D.

The P2' substrate scope for BS149-DM+222P+217H+225N+189W (BS149-DM PHN F189W) and BS149-DM+222P+217H+225N+189W+218D (BS149-DM PHN F189W+N218D) are shown in FIG. 5.

Conclusion

Combination of single positive mutations identified in S2' pocket has an additive effect and further improves the coupling yield and the P2' substrate scope.

Example 3: Mapping of the P2 Pocket Substrate Specificity of Different Enzyme Variants with a Mutation in the P2 Pocket To determine the P2 pocket substrate specificity of the different mutants, the following standard reaction was performed. 800 µL of phosphate buffer (100 mM, pH 8.0) was added to a mixture of 100 µL tripeptide C-terminal amide stock solution (0.01 mmol H-Ala-Leu-Arg-NH$_2$.2TFA in 300 µL water) and 200 µL pentapeptide C-terminal Cam-ester stock solution (0.01 mmol Ac-Asp-Phe-Ser-Xxx-Leu-OCam.TFA in 1.2 mL water+1 mL acetonitrile). Couplings with all these peptide esters were performed, differing in the amino acid at the Xxx position.

To this mixture 5.5 µg enzyme was added and the reaction mixture was shaken (150 rpm) at room temperature. After 30 min a 550 µL aliquot of the reaction mixture was withdrawn and quenched with 500 µL MSA/water (1/99, v/v) and analyzed by LC-MS. The coupling product, the hydrolysed pentapeptide C-terminal Cam-ester and the remaining pentapeptide C-terminal Cam-ester peaks were integrated. The area % product is defined as the amount of product divided by the total of the amount of product, hydrolysed pentapeptide C-terminal Cam-ester and remaining pentapeptide C-terminal Cam-ester, within the specified reaction time.

Figure 3:
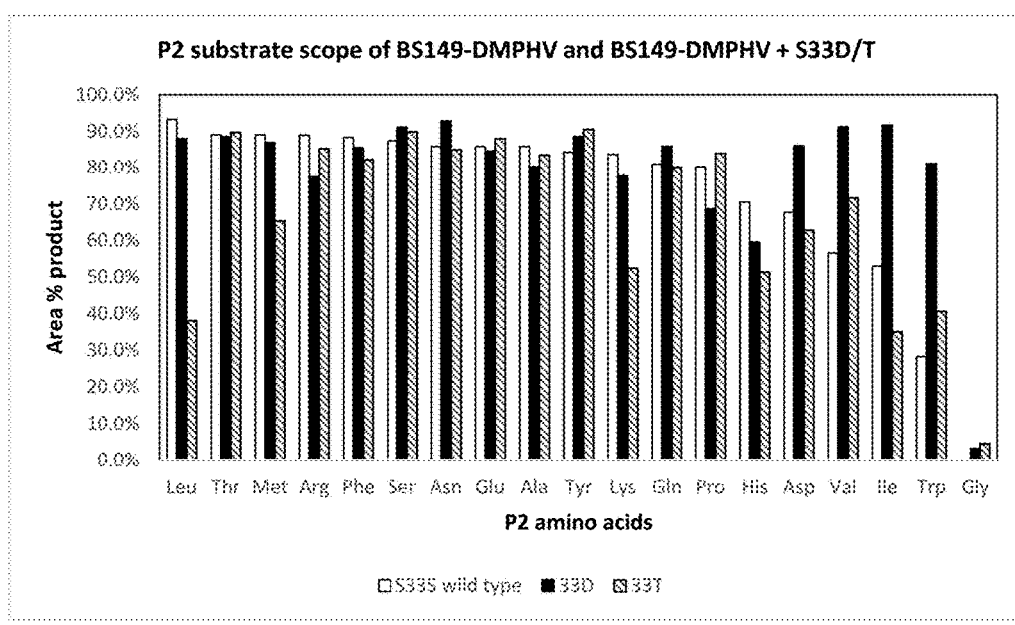
FIG. 3: P2 substrate scope for BS149-DMPHV and BS149-DMPHV+S33D/T.

The P2 substrate scope for BS149-DM+222P+217H+107V (BS149-DMPHV) and BS149-DM+222P+217H+107V+S33D/T (BS149-DMPHV+S33D/T) is shown in FIG. 3.

Figure 4:
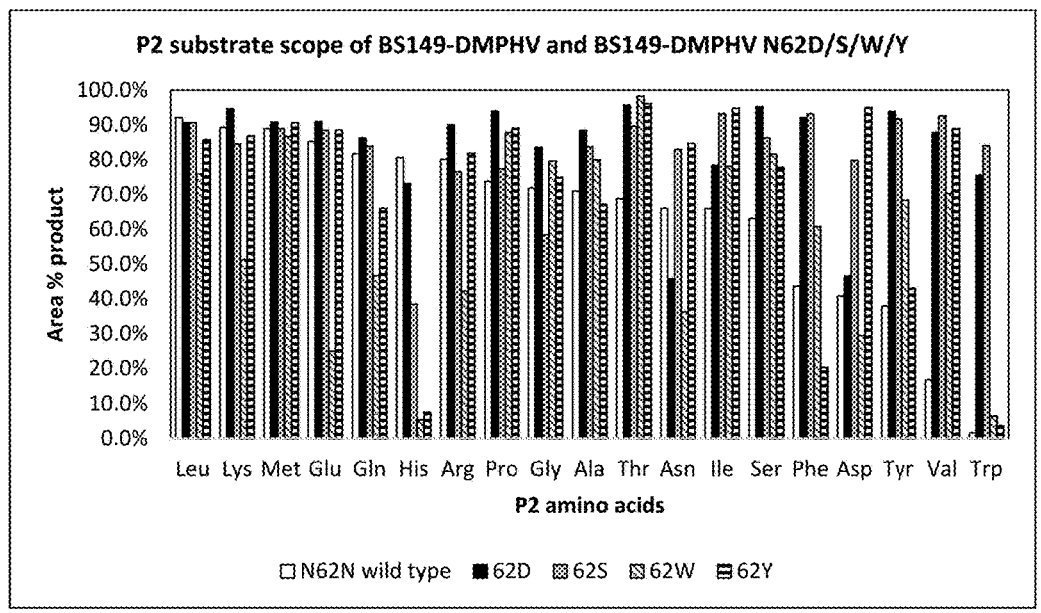
FIG. 4: P2 substrate scope for BS149-DMPHV and BS149-DMPHV+N62D/S/W/Y.

The P2 substrate scope for BS149-DM+222P+217H+107V (BS149-DMPHV) and BS149-DM+222P+217H+107V+N62D/S/W/Y (BS149-DMPHV+N62D/S/W/Y) is shown in FIG. 4.

Conclusions

The mutations S33D and S33T have a positive effect with regards to the P2 substrate scope and coupling efficiency. S33D is better as compared to S33T (FIG. 3). The mutations N62D and N62S have a positive effect with regards to the P2 substrate scope and coupling efficiency. The mutations N62W and N62Y have preferences for a specific set of substrates (FIG. 4).

Example 4: Mapping of the P2 Pocket Substrate Specificity of Different Enzyme Variants with a Mutation in the P2 Pocket To determine P2 pocket substrate specificity of the different mutants, the following reactions were performed. First, the substrate premix (15 µL) was prepared from respective stock solutions in water with final concentrations of 10 mM pentapeptide Cam-ester Ac-Asp-Phe-Ser-Xxx-Leu-OCam.TFA and 10 mM of C-terminal amide H-Ala-Leu-Lys-Lys(DNP)-Lys-NH$_2$.2TFA. To this mixture 50 µL of enzyme solution in 1M Tricine buffer pH 8.5 supplemented with TCEP (tris-(2-carboxyethyl)phosphine hydrochloride, 0.1 mg/ml) was added. In total 0.25 µg enzyme was added per well and the reaction mixture was shaken (150 rpm) at room temperature. After 30 min a 25 µL aliquot of the reaction mixture was withdrawn and quenched with 475 µL MSA/water (2/98, v/v), diluted with 500 µl water and analyzed by LC-MS. The coupling product, the hydrolyzed pentapeptide C-terminal Cam-ester and the remaining pentapeptide C-terminal Cam-ester peaks were integrated. The area % product is defined as the amount of product divided by the total of the amount of product, hydrolyzed pentapeptide C-terminal Cam-ester and remaining pentapeptide C-terminal Cam-ester, within the specified reaction time.

Figure 6:
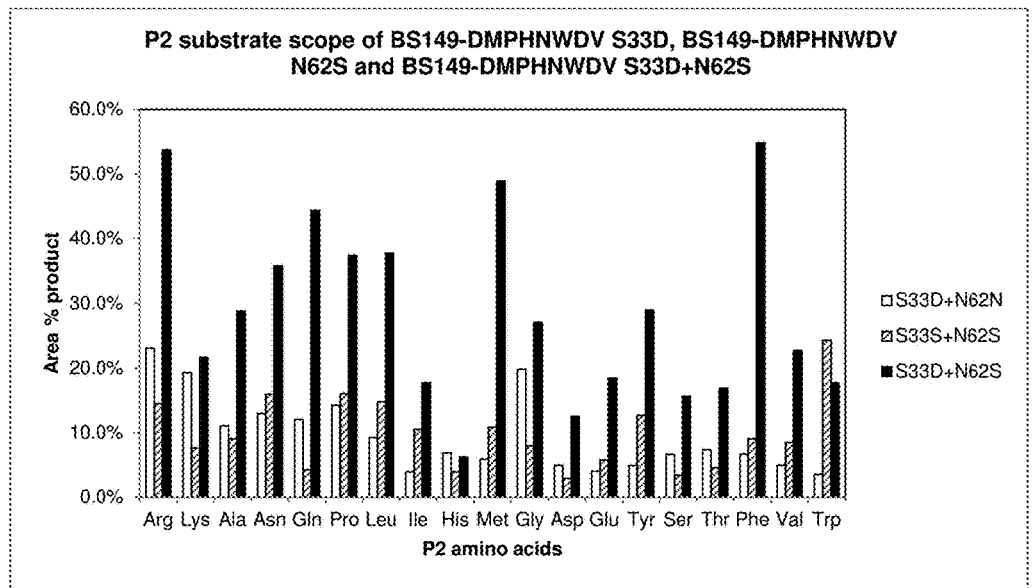
FIG. 6: P2 substrate scope for BS149-DMPHNWDV S33D, BS149-DMPHNWDV N62S and BS149-DMPHNWDV S33D+N62S

The P2 substrate scope for BS149-DM+222P+217H+225N+189W+218D+107V+S33D (BS149-DMPHNWDV S33D), BS149-DM+222P+217H+225N+189W+218D+107V+N62S (BS149-DMPHNWDV N62S) and BS149-DM+222P+217H+225N+189W+218D+107V+S33D+N62S (BS149-DMPHNWDV S33D+N62S) are shown in FIG. 6.

Conclusions

Combination of mutations in S2 pocket (position 33 and 62) shows a clear synergistic effect. Combination of S33D+N62S outperforms single S33D or N62S variant. In addition, the combination mutant also has a distinct specificity profile.

Figure 7:
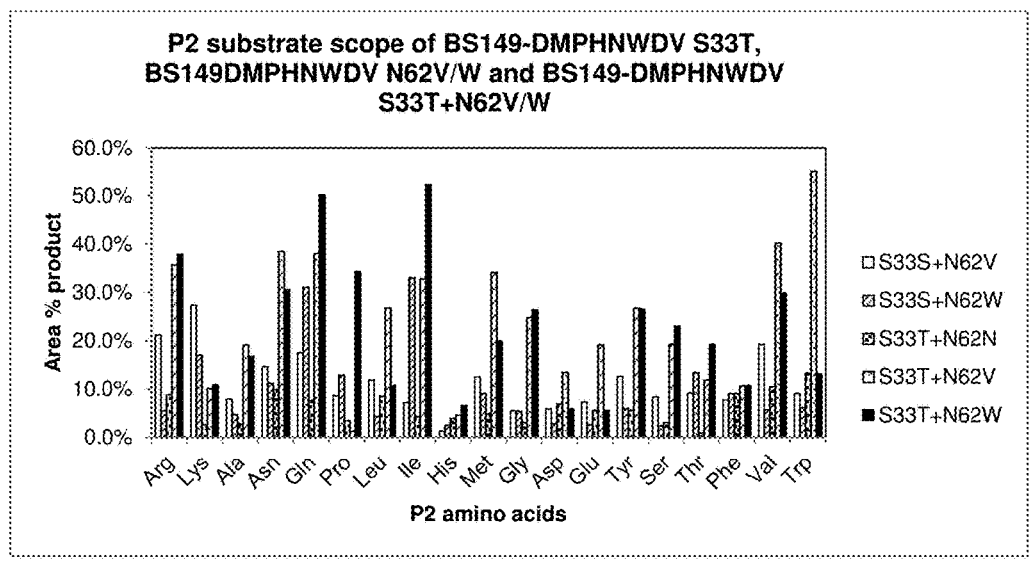
FIG. 7: P2 substrate scope for BS149-DMPHNWDV S33T, BS149-DMPHNWDV N62V/W and BS149-DMPHNWDV S33T+N62W/V

The P2 substrate scope for BS149-DM+222P+217H+225N+189W+218D+107V+S33T (BS149-DMPHNWDV S33T), BS149-DM+222P+217H+225N+189W+218D+107V+N62V/W (BS149-DMPHNWDV N62V/W) and BS149-DM+222P+217H+225N+189W+218D+107V+S33T+N62V/W (BS149-DMPHNWDV S33T+N62V/W) are shown in FIG. 7.

Conclusions

Combination of mutations in position 33 and 62 has synergistic effect with regards to the P2 substrate scope.

Combination of S33T+N62V and S33T+N62W outperforms single S33T, N62V or N62W variant.

Example 5: Synthesis of Exenatide from Two Fragments Using BS149-DMPHV and BS149-DMPHNV+F189W In duplo, 300 mg of H-His$^1$-Gly$^2$-Glu$^3$-Gly$^4$-Thr$^5$-Phe$^6$-Thr$^7$-Ser$^8$-Asp$^9$-Leu$^{10}$-Ser$^{11}$-Lys$^{12}$-Gln$^{13}$-Met$^{14}$-Glu$^{15}$-Glu$^{16}$-Glu$^{17}$-Ala$^{18}$-Val$^{19}$-Arg$^{20}$-Leu$^{21}$-OCam-Leu-OH.3TFA and 200 mg of H-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$-NH$_2$.2TFA were dissolved in 1 mL phosphate buffer (0.2 M) and the pH was adjusted to 8.3 using aqueous NaOH (5 M). To this mixture 100 μL of BS149-DMPHV (1 mg/mL, experiment 1) or 100 μL of BS149-DMPHNV+F189W (1 mg/mL, experiment 2) was added and the reaction mixtures were shaken (200 rpm) at 37° C. After 60 minutes the reaction mixtures were quenched with 9 mL MSA/water (1/9, v/v) and analysed by LC-MS. The Cam-ester starting material, hydrolysed Cam-ester and Exenatide product peaks were integrated. The amount of Exenatide product was 89% (11% hydrolysis) for BS149-DMPHV (experiment 1) and 97% (3% hydrolysis) for BS149-DMPHNV+F189W (experiment 2)

Conclusion

The mutation F189W has a positive effect on coupling efficiency and reaction yield.

Example 6: Synthesis of the Cyclotide McoTI-II Using BS149-DM+222P+217H+225N+107V+189W 1 mg of H-Ile-Leu-Lys-Lys-Cys-Arg-Arg-Asp-Ser-Asp-Cys-Pro-Gly-Ala-Cys-Ile-Cys-Arg-Gly-Asn-Gly-Tyr-Cys-Gly-Ser-Gly-Ser-Asp-Gly-Gly-Val-Cys-Pro-Lys-OCam-Leu-OH was dissolved in 1 mL phosphate buffer (1 M) and the pH was adjusted to 8.3 using aqueous NaOH (5 M). To this mixture 10 μL of BS149-DM+222P+217H+225N+107V+189W (1 mg/mL) was added and the reaction mixture was left to stand at ambient temperature. After 60 minutes the reaction mixture was quenched with 9 mL MSA/water (1/9, v/v) and analysed by LC-MS. The Cam-ester starting material, hydrolysed Cam-ester and cyclic McoTI-II product peaks were integrated. The amount of cyclic product was 93% (7% hydrolysis).

SEQUENCES

SEQ ID NO 1: wild type gene encoding for subtilisin BPN' amino acids -107 to 275
ENA|K02496|K02496.1 B. Subtilisin BPN'
Bacillus amyloliquefaciens
GTGAGAGGCAAAAAAGTATGGATCAGTTTGCTGTTTGCTTTAGCGT

TAATCTTTACGATGGCGTTCGGCAGCACATCCTCTGCCCAGGCGGC

AGGGAAATCAAACGGGGAAAAGAAATATATTGTCGGGTTTAAACAG

ACAATGAGCACGATGAGCGCCGCTAAGAAGAAAGATGTCATTTCTG

AAAAAGGCGGGAAAGTGCAAAAGCAATTCAAATATGTAGACGCAGC

TTCAGCTACATTAAACGAAAAAGCTGTAAAAGAATTGAAAAAAGAC

CCGAGCGTCGCTTACGTTGAAGAAGATCACGTAGCACATGCGTACG

CGCAGTCCGTGCCTTACGGCGTATCACAAATTAAAGCCCCTGCTCT

GCACTCTCAAGGCTACACTGGATCAAATGTTAAAGTAGCGGTTATC

GACAGCGGTATCGATTCTTCTCATCCTGATTTAAAGGTAGCAGGCG

GAGCCAGCATGGTTCCTTCTGAAACAAATCCTTTCCAAGACAACAA

CTCTCACGGAACTCACGTTGCCGGCACAGTTGCGGCTCTTAATAAC

TCAATCGGTGTATTAGGCGTTGCGCCAAGCGCATCACTTTACGCTG

TAAAAGTTCTCGGTGCTGACGGTTCCGGCCAATACAGCTGGATCAT

TAACGGAATCGAGTGGGCGATCGCAAACAATATGGACGTTATTAAC

ATGAGCCTCGGCGGACCTTCTGGTTCTGCTGCTTTAAAAGCGGCAG

TTGATAAAGCCGTTGCATCCGGCGTCGTAGTCGTTGCGGCAGCCGG

TAACGAAGGCACTTCCGGCAGCTCAAGCACAGTGGGCTACCCTGGT

AAATACCCTTCTGTCATTGCAGTAGGCGCTGTTGACAGCAGCAACC

AAAGAGCATCTTTCTCAAGCGTAGGACCTGAGCTTGATGTCATGGC

ACCTGGCGTATCTATCCAAAGCACGCTTCCTGGAAACAAATACGGG

GCGTACAACGGTACGTCAATGGCATCTCCGCACGTTGCCGGAGCGG

CTGCTTTGATTCTTTCTAAGCACCCGAACTGGACAAACACTCAAGT

CCGCAGCAGTTTAGAAAACACCACTACAAAACTTGGTGATTCTTTC

TACTATGGAAAAGGGCTGATCAACGTACAGGCGGCAGCTCAGTAA

SEQ ID NO 2: wild type subtilisin BPN' (mature)
>SUBT_BACAM Subtilisin BPN' Bacillus amyloliquefaciens mature 1 to 275
AQSVPYGVSQIKAPALHSQGYTGSNVKVAVIDSGIDSSHPDLKVAG

GASMVPSETNPFQDNNSHGTHVAGTVAALNNSIGVLGVAPSASLYA

VKVLGADGSGQYSWIINGIEWAIANNMDVINMSLGGPSGSAALKAA

VDKAVASGVVVVAAAGNEGTSGSSSTVGYPGKYPSVIAVGAVDSSN

QRASFSSVGPELDVMAPGVSIQSTLPGNKYGAYNGTSMASPHVAGA

AALILSKHPNWTNTQVRSSLENTTTKLGDSFYYGKGLINVQAAAQ

SEQ ID NO 3: subtilisin BPN' variant with deletion of Ca$^{2+}$ binding loop, S221 mutation (S221X), S33, N62, F189, N218 mutation positions and P225 mutation position
AQSVPYGVSQIKAPALHSQGYTGSNVKVAVIDXGIDSSHPDLKVAG

GASMVPSETNPFQDNXSHGTHVAGTVAAVAPSASLYAVKVLGADGS

GQYSWIINGIEWAIANNMDVINMSLGGPSGSAALKAAVDKAVASGV

VVVAAAGNEGTSGSSSTVGYPGKYPSVIAVGAVDSSNQRASXSSVG

PELDVMAPGVSIQSTLPGNKYGAYXGTXMASXHVAGAAALILSKHP

NWTNTQVRSSLENTTTKLGDSFYYGKGLINVQAAAQ

The invention claimed is:

1. An enzyme, which enzyme is a subtilisin BPN' variant or homologue variant thereof, comprising the following mutations compared to subtilisin BPN' represented by SEQ ID NO: 2 or a homologue sequence thereof:
   a deletion of the amino acids corresponding to positions 75-83;
   a mutation at the amino acid position corresponding to S221, the mutation corresponding to S221C or S221 selenocysteine; and
   at least one further mutation selected from the group consisting of amino acid positions corresponding to F189W, F189Y, S33D, S33T, N218D, N218T, N218E, N62D, N62S, N62W, and N62Y; and
   optionally, a mutation at the amino acid position corresponding to P225;
   wherein the amino acid positions are defined according to the sequence of subtilisin BPN' represented by SEQ ID NO: 2.

2. The enzyme according to claim 1, wherein the S221 mutation is S221C.

3. The enzyme according to claim 1, wherein the at least one further mutation comprises F189W or F189Y.

4. The enzyme according to claim 3, wherein mutation is F189W.

5. The enzyme according to claim 1, wherein the at least one further mutation comprises F189W or F189Y and N218D or N218T.

6. The enzyme according to claim 1, wherein the at least one further mutation comprises N218D, N218T, or N218E.

7. The enzyme according to claim 6, wherein the mutation is N218D.

8. The enzyme according to claim 1, wherein the at least one further mutation comprises S33D or S33T.

9. The enzyme according to claim 8, comprising two further mutations at F189W and N218D, and further comprising the mutations corresponding to M222P, Y217H, P225N, and I107V of SEQ ID NO: 2.

10. The enzyme according to claim 8, wherein the mutation is S33D and said enzyme further comprising at least one further mutation at N62S.

11. The enzyme according to claim 8, wherein the mutation is S33T and said enzyme further comprising at least one further mutation at N62W or N62V.

12. The enzyme according to claim 1, wherein the at least one further mutation comprises N62D, N62S, N62Y, or N62W.

13. The enzyme according to claim 12, wherein the mutation is N62D.

14. The enzyme according to claim 1, wherein at least two further mutations are selected from the group consisting of amino acid positions corresponding to F189W, F189Y, S33D, S33T, N218D, N218T, N218E, N62D, N62S, N62W, and N62Y.

15. The enzyme according to claim 1, wherein at least three further mutations are selected from the group consisting of amino acid positions corresponding to F189W, F189Y, S33D, S33T, N218D, N218T, N218E, N62D, N62S, N62W, and N62Y.

16. The enzyme according to claim 1, wherein at least four further mutations are selected from the group consisting of amino acid positions corresponding to F189W, F189Y, S33D, S33T, N218D, N218T, N218E, N62D, N62S, N62W, and N62Y.

17. The enzyme according to claim 1, comprising a mutation at the amino acid position corresponding to P225 selected from the group of amino acid positions corresponding to P225N, P225D, P225S, P225C, P225G, P225A, P225T, P225V, P225I, P225L, P225H, and P225Q.

18. The enzyme according to claim 16, wherein the mutation at P225 is selected from the group of amino acid positions corresponding to P225N, P225D, P225S, P225C, P225G, P225A, or P225T.

19. The enzyme according to claim 1 further comprising 1-16 mutations selected from the group of mutations at an amino acid position corresponding to Q2, S3, P5, S9, I31, K43, M50, A73, E156, G166, G169, S188, Q206, N212, T254, and Q271 of SEQ ID NO 2, wherein one or more of said mutations are selected from the group of positions corresponding to Q2K, S3C, P5S, S9A, I31L, K43N, M50F, A73L, E156S, G166S, G169A, S188P, Q206C, N212G, T254A, and Q271E.

20. The enzyme according to claim 19, wherein at least six of said mutations are selected from the group of positions corresponding to Q2K, S3C, P5S, S9A, I31L, K43N, M50F, A73L, E156S, G166S, G169A, S188P, Q206C, N212G, T254A, and Q271E.

21. The enzyme according to claim 19, wherein at least twelve of said mutations are selected from the group of positions corresponding to Q2K, S3C, P5S, S9A, 131L, K43N, M50F, A73L, E156S, G166S, G169A, S188P, Q206C, N212G, T254A, and Q271E.

22. The enzyme according to claim 19, comprising 6-15 mutations selected from the group of mutations at an amino acid position corresponding to Q2, S3, P5, S9, I31, K43, M50, A73, E156, G166, G169, S188, Q206, N212, T254, and Q271 of SEQ ID NO 2, wherein one or more of said mutations is selected from the group of positions corresponding to Q2K, S3C, P5S, S9A, I31L, K43N, M50F, A73L, E156S, G166S, G169A, S188P, Q206C, N212G, T254A, and Q271E.

23. The enzyme according to claim 19, comprising 12-14 mutations selected from the group of mutations at an amino acid position corresponding to Q2, S3, P5, S9, I31, K43, M50, A73, E156, G166, G169, S188, Q206, N212, T254, and Q271 of SEQ ID NO 2, wherein one or more of said mutations is selected from the group of positions corresponding to Q2K, S3C, P5S, S9A, I31L, K43N, M50F, A73L, E156S, G166S, G169A, S188P, Q206C, N212G, T254A, and Q271E.

24. A method for enzymatically synthesizing a peptide, comprising coupling (a) a peptide C-terminal ester or thioester and (b) a peptide nucleophile having an N-terminally unprotected amine, wherein the coupling is carried out in a fluid comprising water, and wherein the coupling is catalyzed by an enzyme according to claim 1.

25. The method according to claim 24, wherein the peptide C-terminal ester or thioester or the peptide nucleophile is a protein.

26. The method according to claim 25, wherein the protein is selected from the group consisting of antibodies, antibody-fragments, peptide-based receptor ligands, albumin, biotin, growth factors, hormones, and nanobodies.

27. The method according to claim 24, wherein the peptide C-terminal ester or thioester, the peptide nucleophile, or both, comprise a peptide chain having 2-100 amino acid units.

28. The method according to claim 24, wherein the peptide C-terminal ester or thioester is a conjugate of a peptide C-terminal ester or thioester and a moiety selected from the group consisting of polyalkylene glycols, fatty acids and polysialic acids; and/or the peptide nucleophile is a conjugate of a peptide nucleophile and a moiety selected from the group of polyalkylene glycols, fatty acids and polysialic acids.

29. A method for enzymatically synthesizing a cyclic peptide of at least 12 amino acids, comprising subjecting a peptide C-terminal ester or thioester having an N-terminally unprotected amine to a cyclisation step wherein said cyclization is carried out in a fluid comprising water, and wherein the cyclization is catalyzed by an enzyme according to claim 1.

* * * * *

SEQUENCE LISTING

<160> NUMBER OF SEQ ID NOS: 9

<210> SEQ ID NO 1
<211> LENGTH: 1149
<212> TYPE: DNA
<213> ORGANISM: Bacillus amyloliquefaciens

<400> SEQUENCE: 1

| | |
|---|---:|
| gtgagaggca aaaagtatg gatcagtttg ctgtttgctt tagcgttaat ctttacgatg | 60 |
| gcgttcggca gcacatcctc tgcccaggcg gcagggaaat caaacgggga aaagaaatat | 120 |
| attgtcgggt ttaaacagac aatgagcacg atgagcgccg ctaagaagaa agatgtcatt | 180 |
| tctgaaaaag gcgggaaagt gcaaaagcaa ttcaaatatg tagacgcagc ttcagctaca | 240 |
| ttaaacgaaa aagctgtaaa agaattgaaa aaagacccga gcgtcgctta cgttgaagaa | 300 |
| gatcacgtag cacatgcgta cgcgcagtcc gtgccttacg gcgtatcaca aattaaagcc | 360 |
| cctgctctgc actctcaagg ctacactgga tcaaatgtta agtagcggt tatcgacagc | 420 |
| ggtatcgatt cttctcatcc tgatttaaag gtagcaggcg gagccagcat ggttccttct | 480 |
| gaaacaaatc ctttccaaga caacaactct cacggaactc acgttgccgg cacagttgcg | 540 |
| gctcttaata actcaatcgg tgtattaggc gttgcgccaa gcgcatcact ttacgctgta | 600 |
| aaagttctcg gtgctgacgg ttccggccaa tacagctgga tcattaacgg aatcgagtgg | 660 |
| gcgatcgcaa acaatatgga cgttattaac atgagcctcg gcggaccttc tggttctgct | 720 |
| gctttaaaag cggcagttga taaagccgtt gcatccggcg tcgtagtcgt tgcggcagcc | 780 |
| ggtaacgaag gcacttccgg cagctcaagc acagtgggct accctggtaa ataccttct | 840 |
| gtcattgcag taggcgctgt tgacagcagc aaccaaagag catctttctc aagcgtagga | 900 |
| cctgagcttg atgtcatggc acctggcgta tctatccaaa gcacgcttcc tggaaacaaa | 960 |
| tacgggcgt acaacggtac gtcaatggca tctccgcacg ttgccggagc ggctgctttg | 1020 |
| attcttttcta agcacccgaa ctggacaaac actcaagtcc gcagcagttt agaaaacacc | 1080 |
| actacaaaac ttggtgattc tttctactat ggaaaagggc tgatcaacgt acaggcggca | 1140 |
| gctcagtaa | 1149 |

<210> SEQ ID NO 2
<211> LENGTH: 275
<212> TYPE: PRT
<213> ORGANISM: Bacillus amyloliquefaciens

<400> SEQUENCE: 2

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
        130                 135                 140

Ser Gly Val Val Val Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 3
<211> LENGTH: 266
<212> TYPE: PRT
<213> ORGANISM: Artificial Sequence
<220> FEATURE:
<223> OTHER INFORMATION: subtilisin variant
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid

<400> SEQUENCE: 3

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Xaa Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Xaa Ser His
    50                  55                  60

```
Gly Thr His Val Ala Gly Thr Val Ala Ala Val Ala Pro Ser Ala Ser
 65                  70                  75                  80

Leu Tyr Ala Val Lys Val Leu Gly Ala Asp Gly Ser Gly Gln Tyr Ser
                 85                  90                  95

Trp Ile Ile Asn Gly Ile Glu Trp Ala Ile Ala Asn Asn Met Asp Val
            100                 105                 110

Ile Asn Met Ser Leu Gly Gly Pro Ser Gly Ser Ala Ala Leu Lys Ala
        115                 120                 125

Ala Val Asp Lys Ala Val Ala Ser Gly Val Val Val Ala Ala Ala
130                 135                 140

Gly Asn Glu Gly Thr Ser Gly Ser Ser Ser Thr Val Gly Tyr Pro Gly
145                 150                 155                 160

Lys Tyr Pro Ser Val Ile Ala Val Gly Ala Val Asp Ser Ser Asn Gln
                165                 170                 175

Arg Ala Ser Xaa Ser Ser Val Gly Pro Glu Leu Asp Val Met Ala Pro
            180                 185                 190

Gly Val Ser Ile Gln Ser Thr Leu Pro Gly Asn Lys Tyr Gly Ala Tyr
            195                 200                 205

Xaa Gly Thr Xaa Met Ala Ser Xaa His Val Ala Gly Ala Ala Ala Leu
210                 215                 220

Ile Leu Ser Lys His Pro Asn Trp Thr Asn Thr Gln Val Arg Ser Ser
225                 230                 235                 240

Leu Glu Asn Thr Thr Thr Lys Leu Gly Asp Ser Phe Tyr Tyr Gly Lys
                245                 250                 255

Gly Leu Ile Asn Val Gln Ala Ala Ala Gln
            260                 265

<210> SEQ ID NO 4
<211> LENGTH: 22
<212> TYPE: PRT
<213> ORGANISM: Artificial Sequence
<220> FEATURE:
<223> OTHER INFORMATION: fragment for syntheis of exenatide
<220> FEATURE:
<221> NAME/KEY: MOD_RES
<222> LOCATION: (22)..(22)
<223> OTHER INFORMATION: Ocam-Leu

<400> SEQUENCE: 4

His Gly Glu Gly Thr Phe Thr Ser Asp Leu Ser Lys Gln Met Glu Glu
 1               5                  10                  15

Glu Ala Val Arg Leu Leu
            20

<210> SEQ ID NO 5
<211> LENGTH: 18
<212> TYPE: PRT
<213> ORGANISM: Artificial Sequence
<220> FEATURE:
<223> OTHER INFORMATION: fragment for synthesis of exenatide
<220> FEATURE:
<221> NAME/KEY: MOD_RES
<222> LOCATION: (18)..(18)
<223> OTHER INFORMATION: AMIDATION

<400> SEQUENCE: 5

Phe Ile Glu Trp Leu Lys Asn Gly Gly Pro Ser Ser Gly Ala Pro Pro
 1               5                  10                  15

Pro Ser
```

```
<210> SEQ ID NO 6
<211> LENGTH: 35
<212> TYPE: PRT
<213> ORGANISM: Artificial Sequence
<220> FEATURE:
<223> OTHER INFORMATION: fragment for synthesis of cyclotide McoTI-II
<220> FEATURE:
<221> NAME/KEY: MOD_RES
<222> LOCATION: (35)..(35)
<223> OTHER INFORMATION: OCam-Leu

<400> SEQUENCE: 6

Ile Leu Lys Lys Cys Arg Arg Asp Ser Asp Cys Pro Gly Ala Cys Ile
1               5                   10                  15

Cys Arg Gly Asn Gly Tyr Cys Gly Ser Gly Ser Asp Gly Gly Val Cys
            20                  25                  30

Pro Lys Leu
        35

<210> SEQ ID NO 7
<211> LENGTH: 4
<212> TYPE: PRT
<213> ORGANISM: Artificial Sequence
<220> FEATURE:
<223> OTHER INFORMATION: elongation of the peptide C-terminal
      (thio)ester with 4 amino acid residues
<220> FEATURE:
<221> NAME/KEY: BINDING
<222> LOCATION: (4)..(4)
<223> OTHER INFORMATION: (thio)ester

<400> SEQUENCE: 7

Phe Ser Lys Leu
1

<210> SEQ ID NO 8
<211> LENGTH: 5
<212> TYPE: PRT
<213> ORGANISM: Artificial Sequence
<220> FEATURE:
<223> OTHER INFORMATION: pentapeptide Cam-ester
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: Ocam-Leu

<400> SEQUENCE: 8

Asp Phe Ser Xaa Leu
1               5

<210> SEQ ID NO 9
<211> LENGTH: 5
<212> TYPE: PRT
<213> ORGANISM: Artificial Sequence
<220> FEATURE:
<223> OTHER INFORMATION: pentapeptide
<220> FEATURE:
<221> NAME/KEY: MOD_RES
<222> LOCATION: (4)..(4)
<223> OTHER INFORMATION: DNP
<220> FEATURE:
<221> NAME/KEY: MOD_RES
<222> LOCATION: (5)..(5)
```

```
<223> OTHER INFORMATION: AMIDATION

<400> SEQUENCE: 9

Ala Leu Lys Lys Lys
1               5
```